United States Patent [19]

Benjamin et al.

[11] Patent Number: 4,793,825
[45] Date of Patent: Dec. 27, 1988

[54] ACTIVE SILICON IMPLANT DEVICES

[75] Inventors: John D. Benjamin, Malvern; Adrian L. Mears, Cheltenham; John C. White, Lincoln, all of England

[73] Assignee: The Secretary of State for Defence in Her Majesty's Government of the United Kingdom, London, England

[21] Appl. No.: 774,691

[22] Filed: Sep. 11, 1985

[30] Foreign Application Priority Data

Sep. 11, 1984 [GB] United Kingdom ................. 8422876

[51] Int. Cl.$^4$ .............................................. A61M 1/00
[52] U.S. Cl. ................................ 604/891.1; 604/145; 128/631; 128/736
[58] Field of Search ................. 128/419 PS, 630, 631, 128/632, 635, 642, 653–654, 659–660, 736, 903; 604/66, 140, 145, 148, 131, 891; 252/1, 600; 374/100, 148, 178; 324/438

[56] References Cited

U.S. PATENT DOCUMENTS

| 3,659,615 | 5/1972 | Enger | 128/419 PS |
|---|---|---|---|
| 3,672,352 | 6/1972 | Summers . | |
| 3,962,412 | 6/1976 | Wolfangel . | |
| 4,003,379 | 1/1977 | Ellinwood, Jr. | 128/DIG. 1 |
| 4,115,536 | 9/1978 | Rothman et al. . | |
| 4,310,505 | 1/1982 | Baldeschwieler . | |
| 4,351,337 | 9/1982 | Sidman . | |
| 4,494,950 | 1/1985 | Fischell | 128/903 X |
| 4,507,115 | 3/1985 | Kantfara et al. | 604/891 X |

FOREIGN PATENT DOCUMENTS

| 340038 | 11/1977 | Australia . |
|---|---|---|
| 356288 | 4/1980 | Australia . |
| 356821 | 5/1980 | Australia . |
| 7656 | 11/1980 | Australia . |
| 367292 | 6/1982 | Australia . |
| 0000667 | 7/1978 | European Pat. Off. . |
| 0042249 | 12/1981 | European Pat. Off. . |
| 109081 | 10/1960 | Fed. Rep. of Germany . |
| 2548838 | 5/1977 | Fed. Rep. of Germany . |
| 2941363 | 4/1981 | Fed. Rep. of Germany . |
| 1528265 | 10/1978 | United Kingdom . |
| 1545271 | 5/1979 | United Kingdom . |
| 1551792 | 8/1979 | United Kingdom . |
| 8301738 | 5/1983 | World Int. Prop. O. . |

OTHER PUBLICATIONS

Harrison, H. B. et al., "Microminiature Transducers for Biomedical Applications", MBE vol. 19, No. 3, May 1981, pp. 362–366.

Sweeney, J. D. et al., "An Implantable Micropower Command Receiver for Telemetry Battery Power Switching", Biotel, Ptnt Monitoring 8: No. 3, pp. 173–179, (1981).

Primary Examiner—Francis J. Jaworski
Attorney, Agent, or Firm—Cushman, Darby & Cushman

[57] ABSTRACT

A medical implant for injecting into the vascular system of animals comprises a device less than 500 μm in size carrying signal processing means for providing an output in response to an input signal. The input may be acoustic, electromagnetic, temperature, pH value, or chemical. The output may be acoustic, electromagnetic, or chemical. Large numbers, e.g., $10^8$, of the implant devices may be mixed into a saline solution and injected into a blood vessel where they are carried around the vascular system, or the devices may be mixed with a gas and inhaled. The amount of circulation depends on the device size. For the larger device e.g., above 7 μm to around 250 μm, circulation will be short lived. Smaller sized e.g., <3 μm devices will circulate for a considerable time. Anti-bodies may be coated onto the devices to cause them to adhere to target areas such as tumors. In one device a chemical is released when illuminated externally by an acoustic beam. In another device a chemical is released when the pH of surrounding blood changes to a given level. Power to operate the device may be by an integral battery.

28 Claims, 19 Drawing Sheets

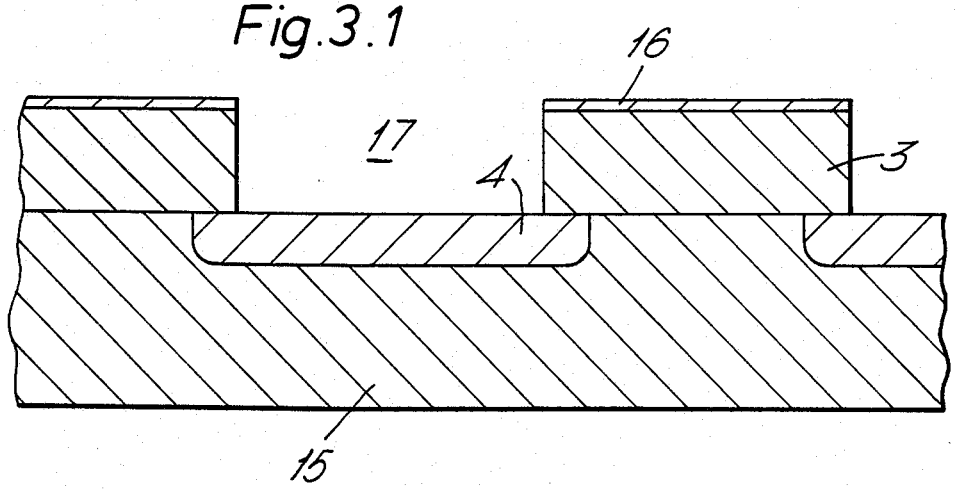
Fig.3.1
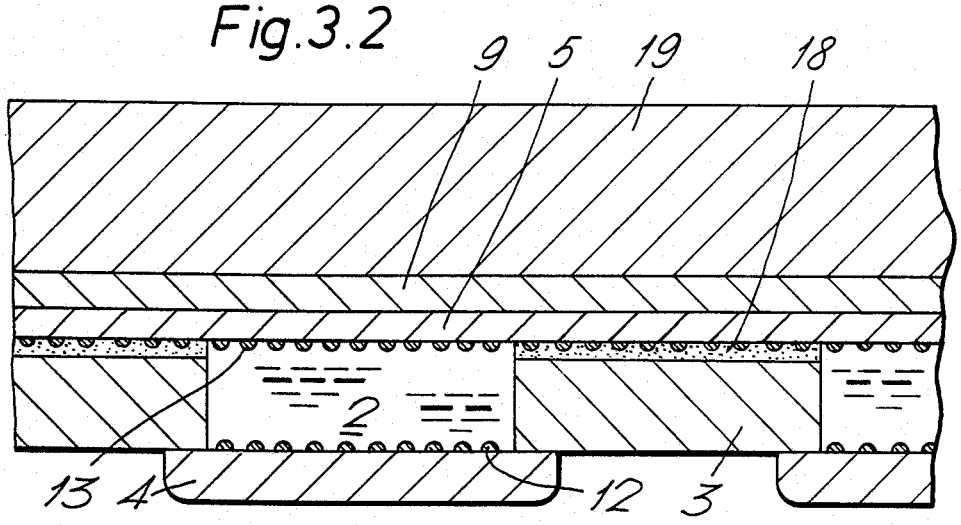
Fig.3.2

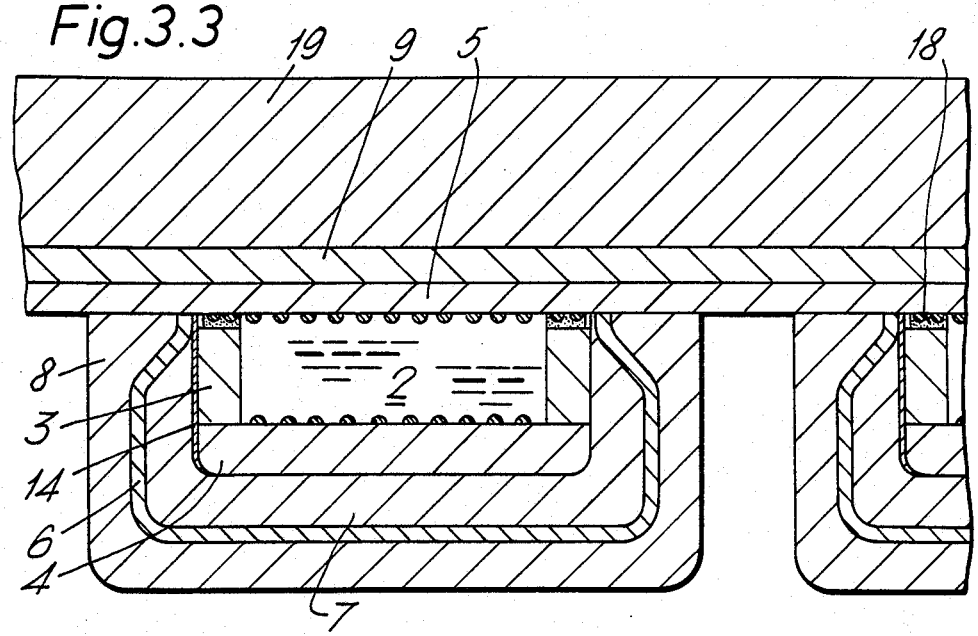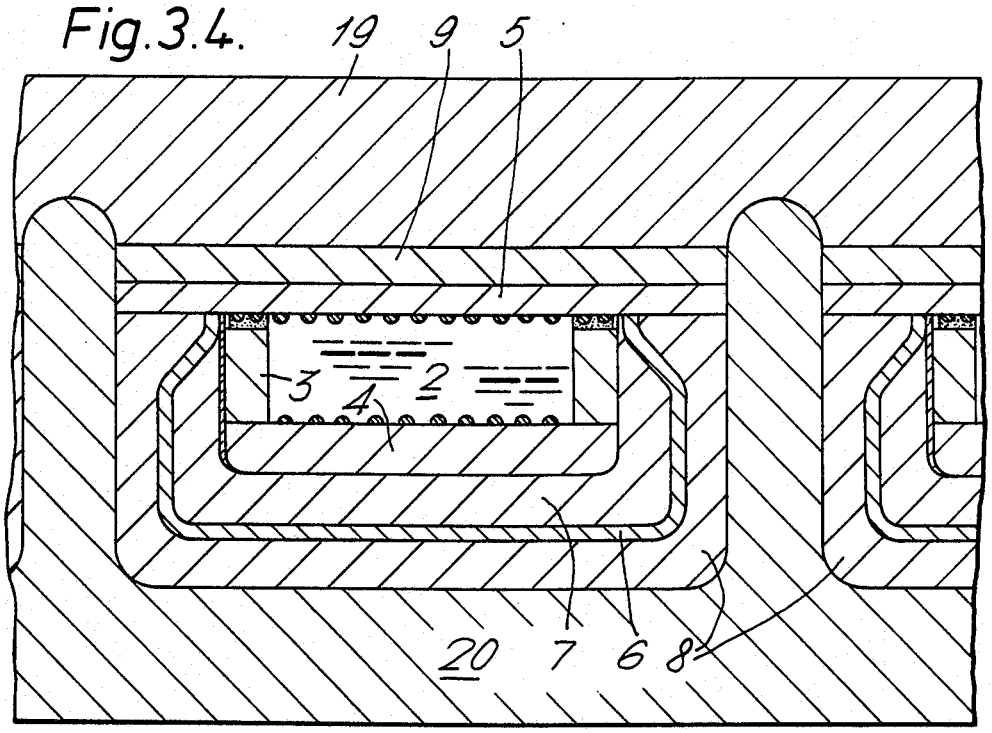

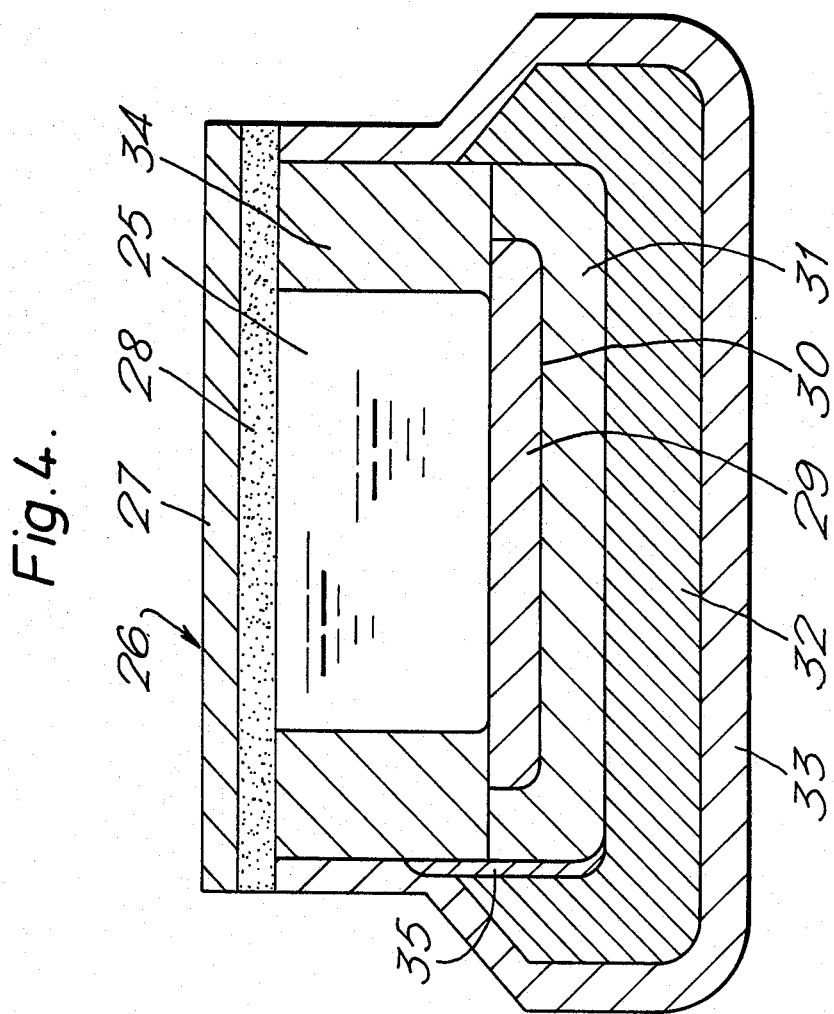

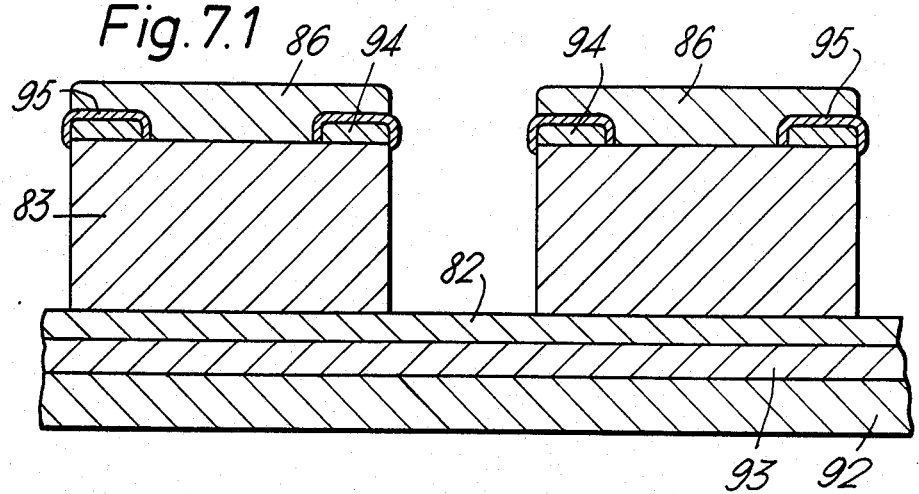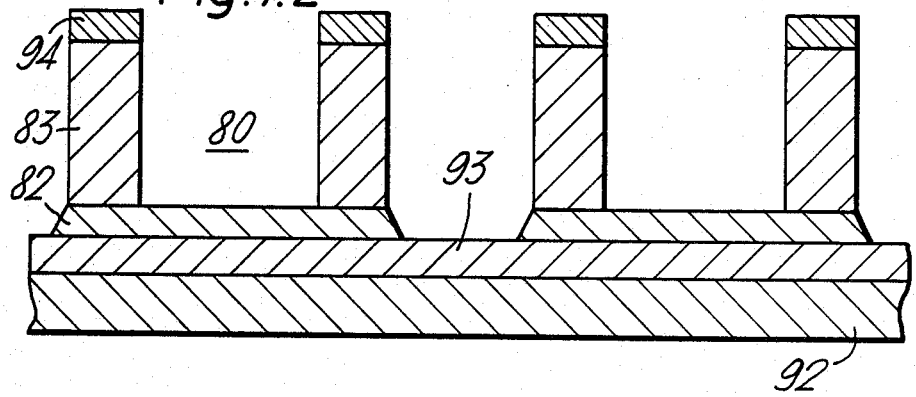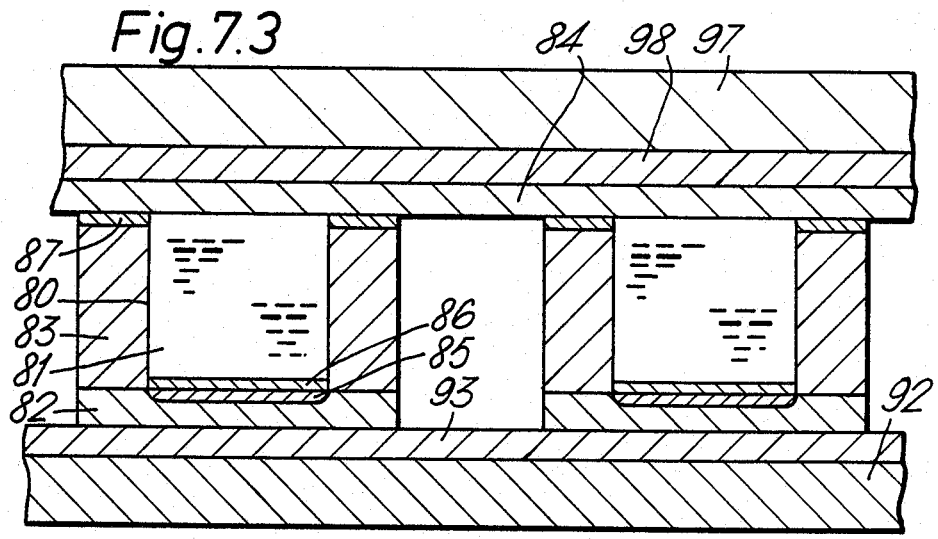

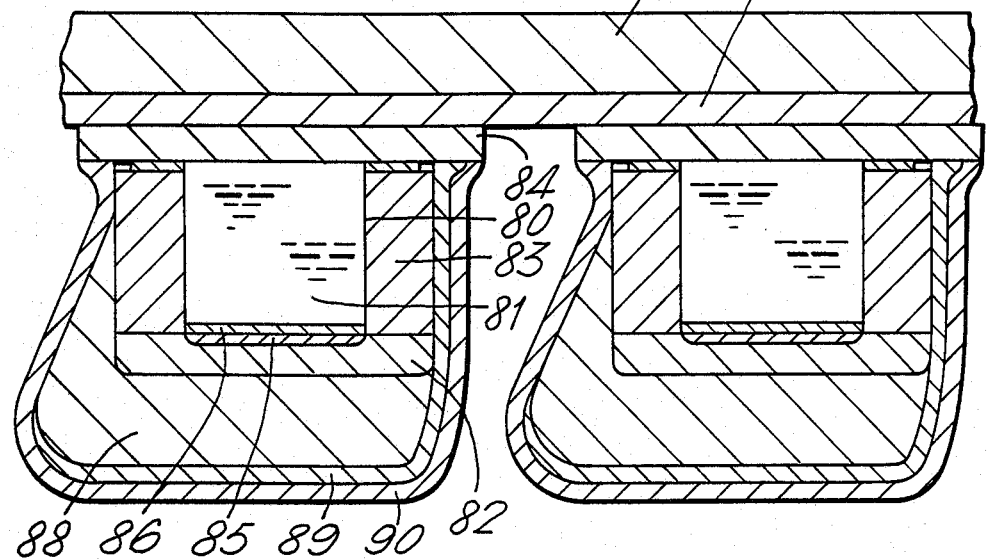
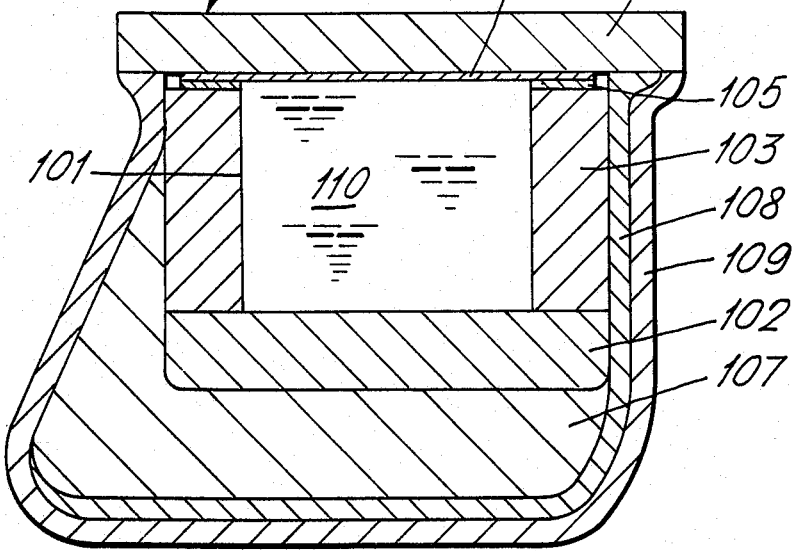

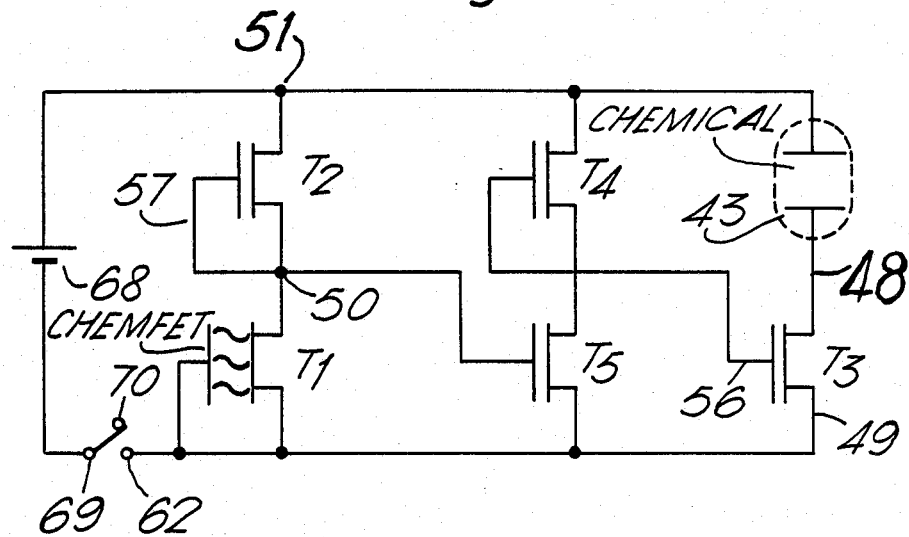
Fig. 10.
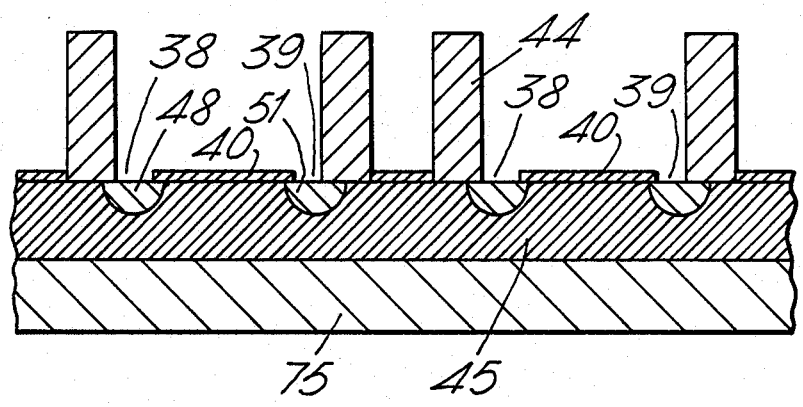
Fig. 11.1

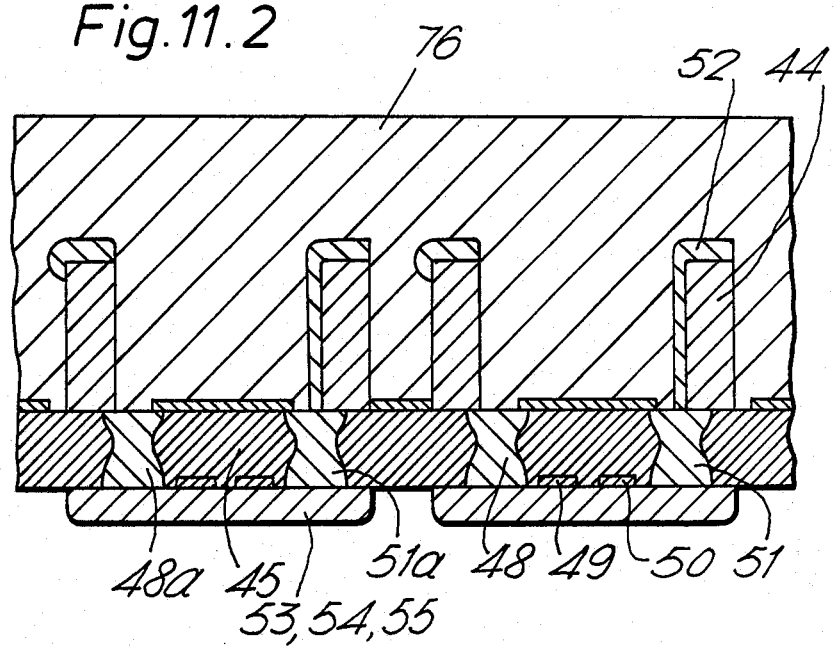
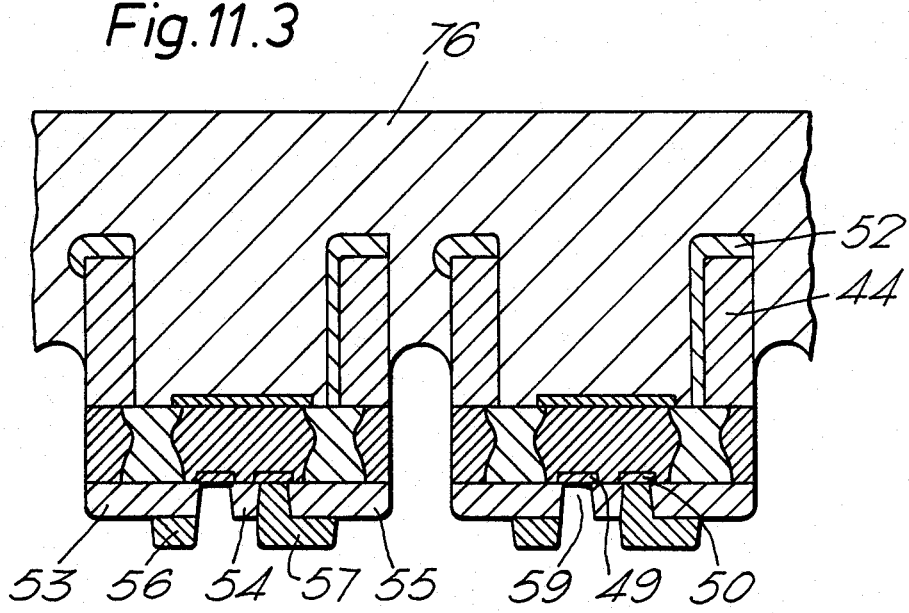

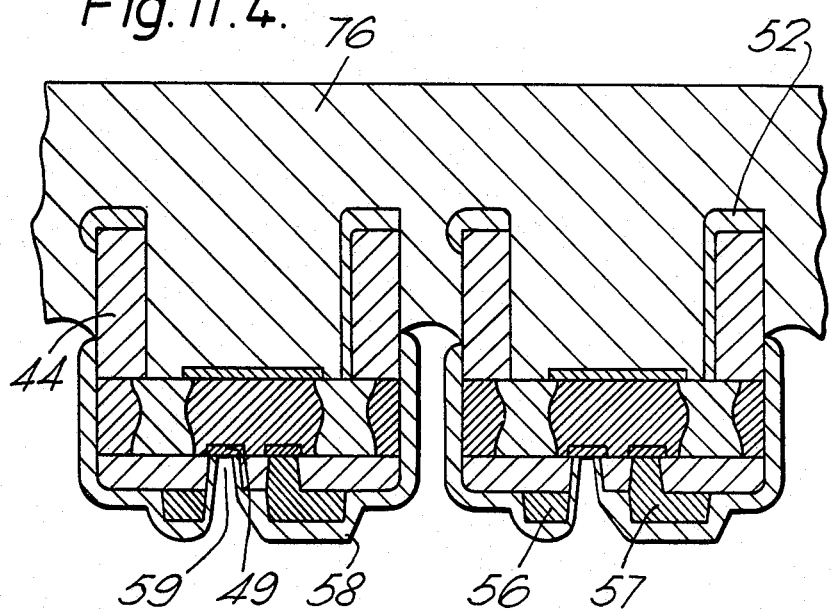
Fig. 11.4.
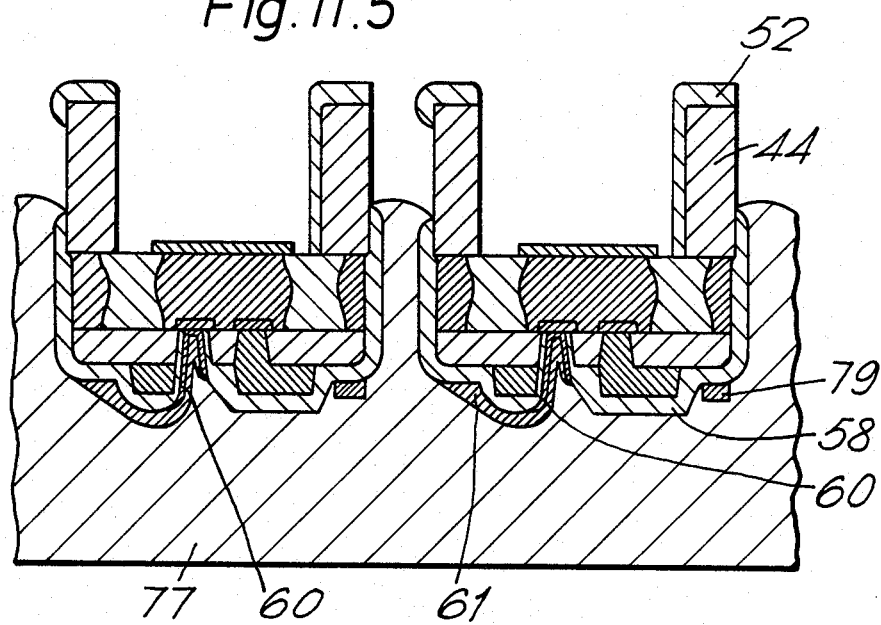
Fig. 11.5

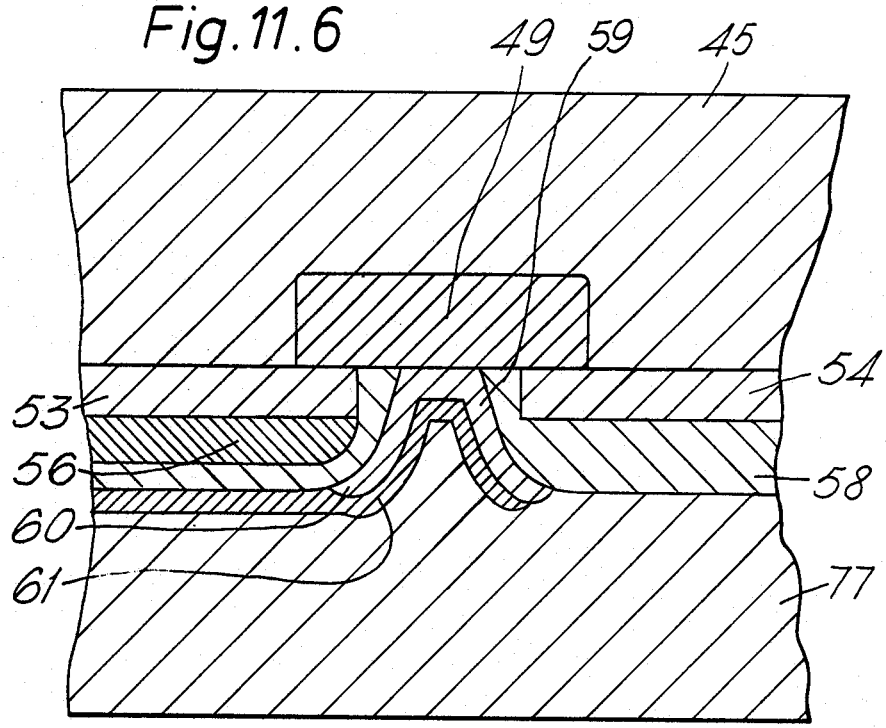
Fig. 11.6
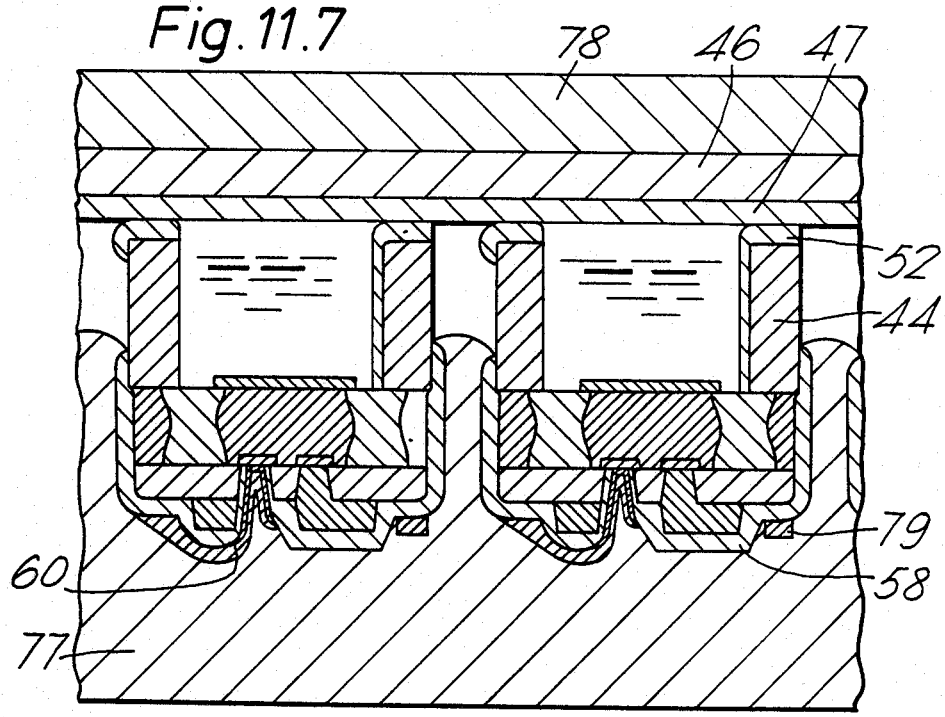
Fig. 11.7

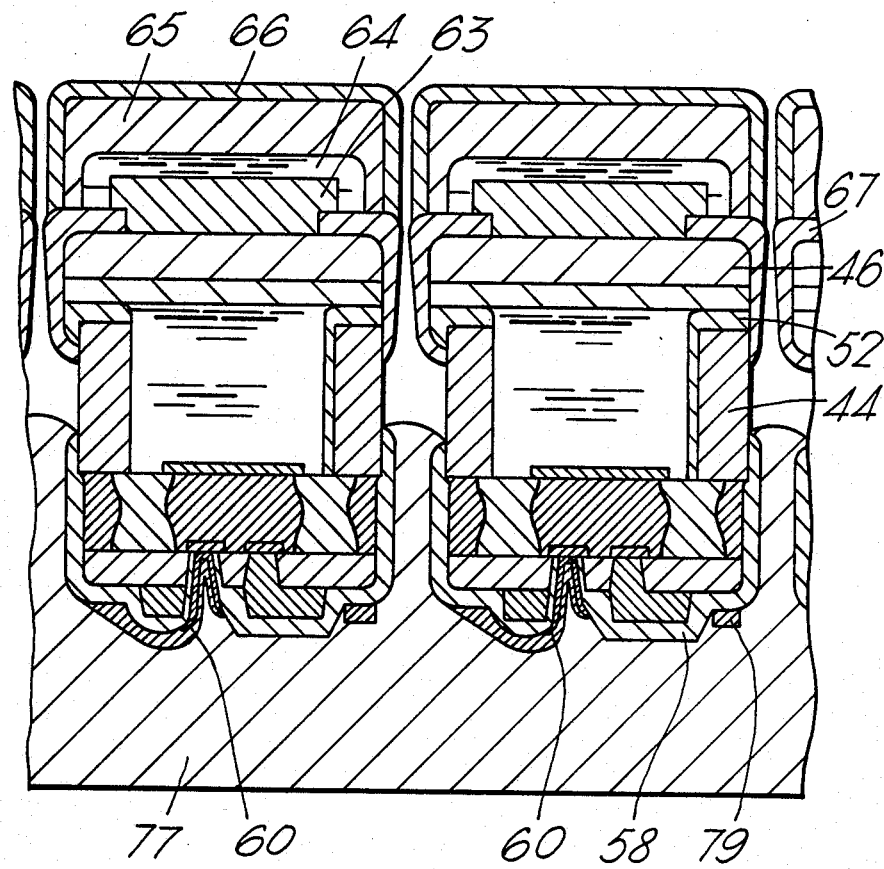
Fig.11.8

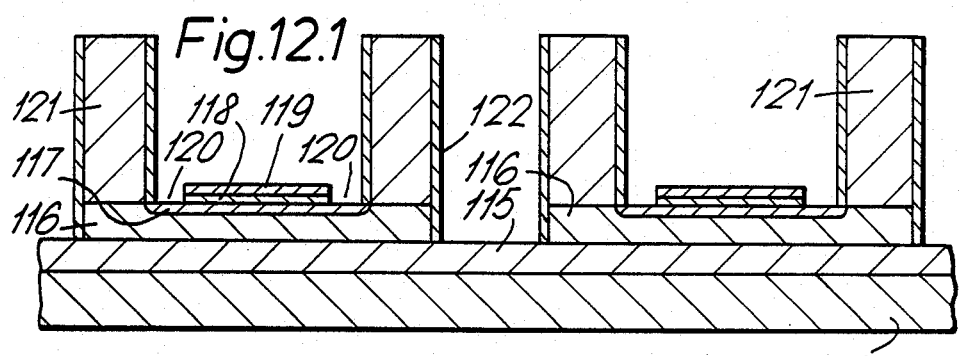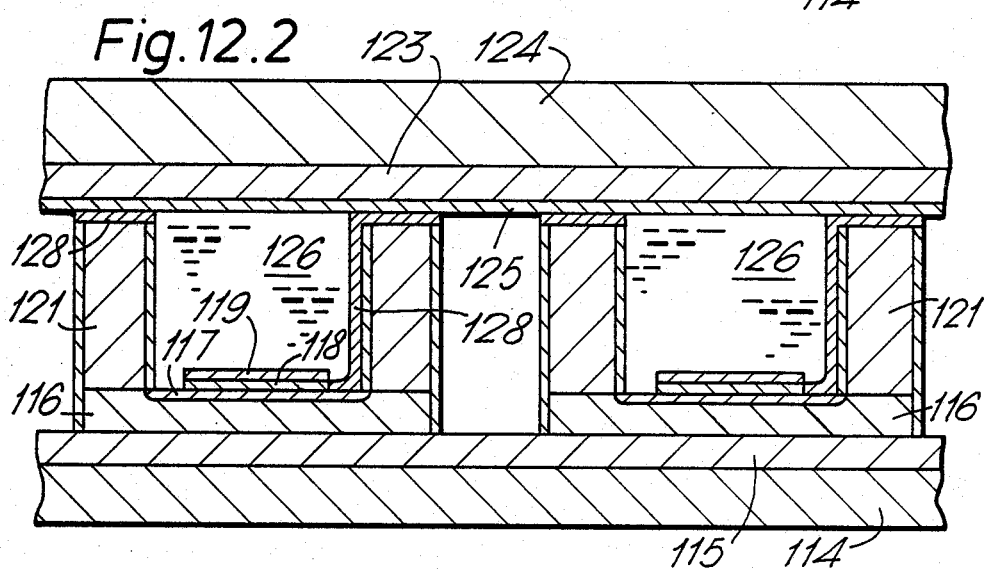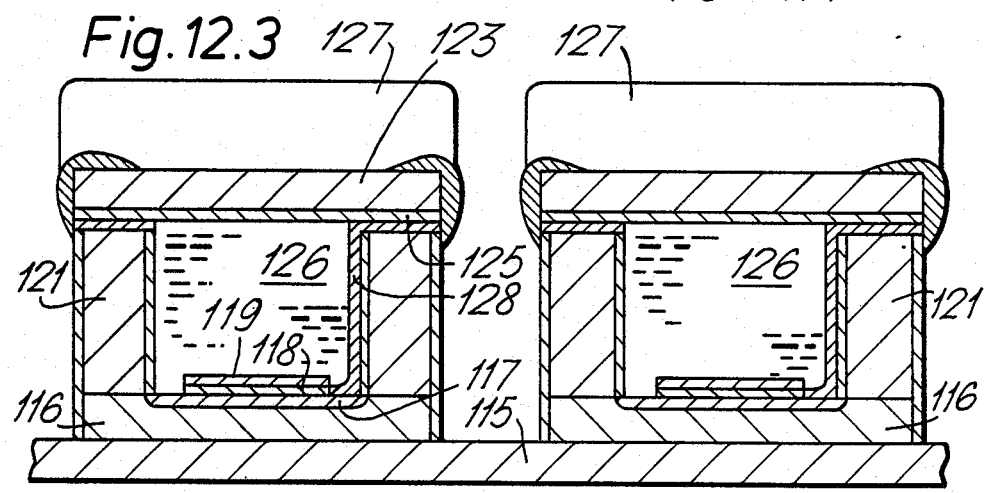

ACTIVE SILICON IMPLANT DEVICES

BACKGROUND OF THE INVENTION

This invention relates to silicon devices for implanting into animals, including humans.

FIELD OF THE INVENTION

Various devices have been used for implants. For example, heart pacemakers are used to maintain an adequate heart beat rate in humans. These can be self contained and are implanted under a surgical operation in the chest cavity where they remain until they are replaced after months or years.

Probes carrying devices have been temporarily inserted into animals to monitor temperature etc. These are short term uses and intrusive.

Small spheres have been injected into the blood stream and their progress monitored. For example 10 to 25 μm diameter spheres have been labelled with a radio nuclide and their movement used in checking blood flow. Such spheres are passive and can only move with blood flow and in some cases release chemicals by dissolving.

Lyposomes, almost invariably submicron in size and incorporating drugs have been employed therapeutically notably in the treatment of leishmaniasis. Again, these devices are wholly passive. These problems are overcome in the present invention by using very small discrete active devices which are injected into the blood circulation to collectively perform a required function such as drug release or temperature monitoring. As an alternative to injection directly into blod vessels, the devices may be inhaled and absorbed into the lungs for circulation within the vascular system, or injected into joints, the cerebral ventricles, and the urinary and genital tracts.

SUMMARY OF THE INVENTION

According to this invention a medical implant comprises a small silicon device, less than 500 μm, capable of passing along blood vessels or of inhalation into the lungs, and carrying signal processing means for providing an output in reponse to an input signal.

For circulation in the blood system the devices are preferably less than 7 μm e.g. <3 μm. For limited circulation within the large blood vessels the device may be 250 μm or more depending upon where the devices are injected.

The input signal may be acoustic, electromagnetic, temperature, nuclear radiation, pH, or chemical.

The output signal may be acoustic, electromagnetic, explosive, or chemical.

Energy to operate the device may be from a battery on the device or external such as acoustic or electromagnetic in co-operation with piezoelectric material or an aerial on the chip.

BRIEF DESCRIPTION OF THE DRAWINGS

The invention will now be described, by way of example only, with reference to the accompanying drawings of which:

FIGS. 3.1 to 3.4 are sectional views showing the processing steps in the production of the device of FIG. 1;

FIG. 4 is a sectional view of an alternative device for carrying a chemical to be released on receipt of an acoustic signal;

FIGS. 7.1 to 7.4 are sectional views showing the processing steps in the production of the device of FIG. 5;

FIG. 8 is an alternative to FIG. 5;

FIG. 10 is a circuit diagram for the device of FIG. 9;

FIGS. 11.1 to 11.8 are sectional views showing processing steps to the production of FIG. 9;

FIGS. 12.1 to 12.3 are sectional views showing alternative processing steps;

DETAILED DESCRIPTION OF THE PREFERRED EMBODIMENT

Figure 1:
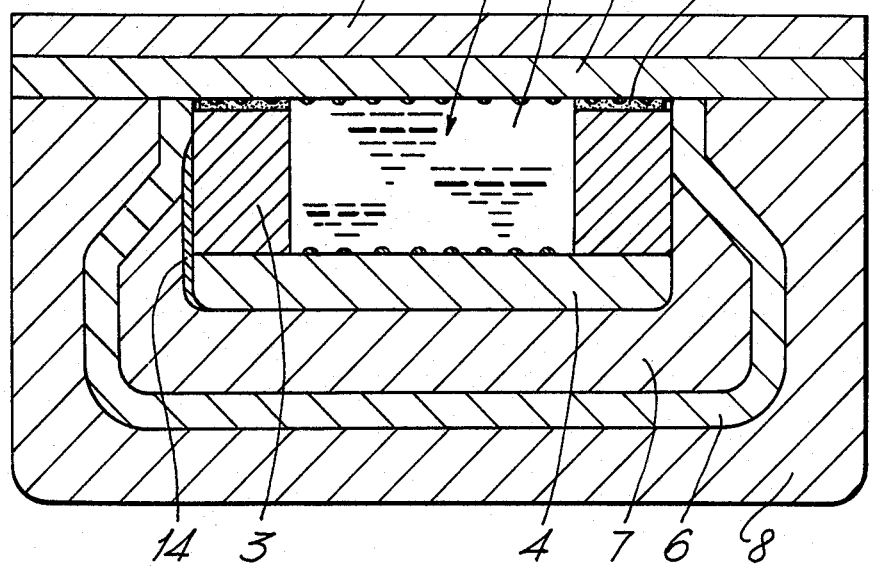
FIG. 1 is a sectional view of a device for carrying a chemical to be released on receipt of an acoustic signal.

The device 1 of FIG. 1 comprises a closed chamber carrying a chemical 2. This chamber is formed by walls 3 of $SiO_2$, a bottom p+ Si plate 4 and a top n-type Si plate 5. A layer 6 of Ti makes electrical contact with the n top plate 5 and encloses a layer 7 of piezo electric material e.g. ZnO. The Ti layer 6 is surrounded by a passivating layer 8 of $SiO_2$ whilst the n top plate 5 is covered by a p+ Si layer 9. A cermet resistor 14 connects the p+Si plate and the titanium plate of the piezo electric material 7.

Figure 2:
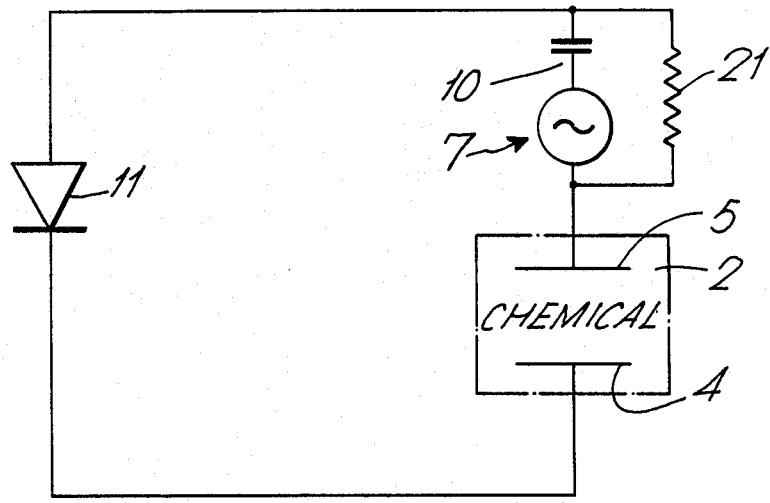
FIG. 2 is a circuit diagram for the device of FIG. 1.

As seen in FIG. 2 the chemical is held between conducting plates 4 and 5. An a/c voltage is generated in the piezo electric 7 when it is illuminated by an acoustic beam. The output impedance of the piezo electric is capacitive so in order to provide a source 10 which can pass a net current a resistance 21 corresponding to the conducting path 14 is placed in parallel with the piezoelectric material 7. The junction between Ti layer 6 and n top plate 5 forms a rectifying diode 11 which passes a d.c. electric current through the chemical 2. This electrolyses the chemical 2 causing gas to be generated which ruptures the cell top plate 5, 9 allowing the chemical to escape.

In view of the small size of the devices the illuminating ultrasound beam must be of very high intensity in order to generate an adequate voltage. In order to achieve this without heating the tissue too much or producing streaming or cavitation effects the ultrasound consists of very short (e.g. 5 μs) pulses of very high intensity sound repeated at regular intervals (e.g. 10 ms).

For treatment in the body of a human about $10^8$ of the FIG. 1 devices are mixed into about 10 cc of a saline solution and injected into a suitable blood vessel. The blood flow causes the devices to be carried along with the blood corpuscles. When they reach the desired place in the body they are illuminated by a beam of acoustic energy eg at $2 \cdot 10^6$ Hz. This causes release of the chemical at a highly localised position in the body. The blood flow may be normal, and go right around the body or blood containing the particles may be artificially circulated round specific organs or regions of the body. The latter approach requires surgery but has the advantage that the flow can then avoid the lung, liver and spleen where significant trapping occurs.

Alternatively the devices can be diluted into a carrier gas, such as a fluorinated hydrocarbon of chain length of typically 11 or 12 (obtainable from I.C.I. Ltd., England), and inhaled. Provided the devices are within the range $<10$ μm they will remain in the lung for absorption into the blood vessels. Larger devices e.g. up to 300 μm can also be inhaled into the lungs.

Enhanced positioning of the devices can be achieved when treating tumours. In this case the devices are coated with an antibody tailored to attach itself to the tumour site only. Antibodies are prepared from cultured samples of the tumour. Examples are P.L.A.P. (placental alkaline phosphatase), H.M.F.G. (human milk fat globulin), C.E.A. (Carcino Embryonic Antibody), H.C.G. (human chorionic gonadotrophin).

When coated with an antibody the devices 1 readily attach themselves to the tumour site as they flow along the adjacent blood vessels and capillaries. After a sufficient number have attached, a time dependent value, they are illuminated by the acoustic beam to release the chemical. By this means very high localised drug dosages can be achieved, much higher than can be tolerated by the body as a whole.

Coating the devices with anti-bodies may also be used for treatment against bacteria. In this case the chemical 2 carried by the device may be gentomycin. Similarly antibody coated devices attach themselves to bacteria and deliver very high local drug concentrations.

The device of FIG. 1 is formed by a series of steps illustrated in FIGS. 3.1 to 3.4.

1. A layer 3, 1.5 μm thick of silicon oxide is grown on an n-type Si substrate 15 of doping density $<10^{19}$ cm$^{-3}$. The oxide layer 3 is grown e.g. by flowing steam over a heated substrate.

2. A layer 16 of photo resist e.g. Shipley AZ1470 obtainable from Shipley Chemicals Ltd. of Herald Way, Conventry CV3 2RQ, is spun onto the SiO$_2$ layer 3 and dried. This resist 16 is exposed through a mask using ultraviolet light. Unexposed resist is dissolved in a developer obtainable from Shipley Chemicals Ltd. Alternatively an electron beam resist such as P.M.M.A. can be used. After exposure with an e beam it can be developed using a 1:1 mixture of isobutyl methyl ketone and isopropyl alcohol.

3. Using the remaining resist as a mask the oxide 3 is removed using a plasma etch. This leaves a series of holes 17 in the oxide 3, FIG. 3.1, typically 1.5 μm square.

4. The remaining resist 16 is removed by immersion in fuming nitric acid or an oxygen plasma and rinsing with deionised water and dried.

5. A layer 4 of p+ Si is formed in the Si substrate 15 at the bottom of each hole 17 for example by diffusion of boron. The layer 4 is typically 0.3 μm thick with a doping concentration of $2.5 \cdot 10^{20}$ cm$^{-3}$.

6. A discontinuous layer 12 of Pt may be deposited e.g. by electron beam evaporation or sputtering on the exposed p+ layer 4 in the holes 17. This Pt layer reduces the voltage subsequently needed to operate the device.

7. The top surface of SiO$_2$ is covered with a thin layer of glue 18 for example by evaporation or printing. Suitable glues are indium evaporated on the oxide, an epoxy resin, or rubber adhesive printed onto the oxide.

8. An upper wafer 19 is prepared of n-type Si typically having a carrier concentration of $<10^{19}$ cm$^{-3}$.

9. This upper wafer 19 has formed thereon a p+ layer 0.2 μm thick 9 followed by an n-layer 5 of 0.2 μm. These layers 9, 5 may be formed by vapour phase epitaxial growth using dopants of arsenic for the n-layer and boron for the p+ layer. Typical doping levels are $5 \cdot 10^{17}$ cm$^{-3}$ for the n layer and $2 \cdot 10^{20}$ cm$^{-3}$ for the p+ layer.

10. A discontinuous Pt 13 film may be deposited on the n layer.

11. A chemical 2 is deposited in each device hole 17 by pouring a liquid over the whole substrate and spinning or blotting off excess chemical or squeezing out the excess when the upper wafer is fixed to the lower wafer. Possible chemicals to attack a tumour are toxins such as nitrogen mustard, the toxin secreted by corynebacterium diphtheriae or rycin. A surfactant may be added to help the chemical into the holes.

12. The upper wafer 19 is placed over the bottom substrate, FIG. 3.2, with the n layer 5 in contact with the glued surface of the oxide. Additional to or instead of glue 18 on the oxide 3 the n layer may be coated with a glue or a hardener for the glue. Pressure is applied to seal the contacting surfaces. When the glue 18 is an epoxy it must be electrically conducting, e.g. by containing metallic powder, or be removed in the area of the chemical so that the n layer 5 makes electrical contact with the chemical 2.

The n layer 5, oxide 3, and p+ layer 4 form closed chambers containing the chemical 2. One apparatus, not shown, for pressing the upper wafer 19 onto the substrate 15 comprises a hydraulic press. Jaws on the press are slightly curved to exert maximum pressure at the centre of the wafer and to squeeze out sideways excess chemical. The upper wafer 19 is placed over the substrate 15, after holes 17 are filled with chemicals, both placed between deformable sheets e.g. 50 μm thick polyethylene, and inserted between the press jaws. As the jaws are brought together excess chemical is squeezed out and the layer 5 bonded firmly to the walls 3.

13. The lower n-type substrate 15 is removed by a selective etch such as EDA or alcoholic KOH (eq), FIG. 3.2. This leaves islands of p+ Si 4 on the SiO$_2$3. This is described in N. F. Raley et al, J. Electrochem. Soc.: Solid State Science, Technology, January 1984, 131(1) pp. 161-171; K Petersen, Proc. I.E.E.E., May 1982 70(5) pp 420-457; and "Thin Film Processes" edited by J. L. Vossen, W. Kern, Academic Press 1978 pp 443-444.

14. Using the p+ Si islands 4 as a mask the exposed oxide is removed with a plasma etch. This etching is stopped when the n Si material 5 is reached, FIG. 3.3, leaving the chamber walls 3 of oxide about 0.5 μm thick.

15. Any glue 18 on the exposed n type layer 5 is removed by etching, e.g. oxygen plasma for an epoxy glue, or dilute hydrochloric acid wet etch for indium glue. For an electrically conducting glue it is advisable to etch it back under the oxide 3 to a small amount. This prevents short circuits to the chemical from any metal layer deposited subsequently.

16. Piezo electrical material 7, e.g. ZnO, is evaporated or sputtered onto the exposed p+ Si and oxide walls, FIG. 3.3. The $ZnO_2$ is deposited at an angle so as not to cover the n layer 5. Since the current which electrolyses the chemical 2 must pass through the zinc oxide 7, either the zinc oxide 7 must leak or a parallel conducting path across it must be provided e.g. by evaporating or sputtering a thin cermet film 14. The resistance of the film 14 must be accurately controlled since if it is too low the piezo electric will be short circuited and if it is too high it will impede the flow of electrolysing current excessively. A typical resistance value is approximately 5/w.C. where w is angular frequency of illuminating ultra sound and C is capacitance of piezo electric layer.

17. An 0.1 μm layer 6 of Ti is evaporated over the $ZnO_2$ and exposed oxide walls 3 and onto the n layer 5 at its junction with the oxide 3. This is achieved by evaporating at an angle.

18. A passivating layer 8 of $SiO_2$ is evaporated or sputtered over the Ti 6 and part of the n layer 5 whilst still leaving exposed parts of n material, FIG. 3.3.

19. The exposed Si, n and p+, 5, 9, is etched through to the n-type Si 19 using the passivating oxide 8 as a mask and KOH or EDA or a plasma as the etchant, FIG. 3.4.

20. A wax or polymer e.g. APIEZON W.40 wax, coating 20 is flowed over the separate devices to provide support, FIG. 3.4.

21. The top n-type Si 19 is removed by a selective etch e.g. EDA or alcoholic KOH which does not etch the p+ material 9. Each device 1 is now separate and held together only by the wax 20.

22. When required the wax or polymer binder 20 is dissolved away to provide unattached devices.

23. If required the separate devices can be coated with an antibody, at least on the passivating oxide.

Details of techniques for coating solid surfaces with antibodies are contained for example in the following together with their associated references:
H. H. Weetall Meth Enzymol 44 p 134
R. A. Messing Metch Enzymol 44 p 148
P. J. Halling & P. Dunnill, Biotechnology and Bioengineering Vol XXI p 393–416 (1979)

In addition to direct coating of the surfaces, the surfaces can be coated with a liquid layer to which antibodies can be attached, as described in
T. D. Heath, R. T. Fraley, D. Papahadjopoulos, Science 210 pp. 539–541 (1980)
A. Huang, Y. S. Tsao, S. J. Kennel, L. Huang, Biochem. Biophys. Act 716, pp 140–150 (1982)
J. Barbet, P. Macky, L. D. Leserman, J. Supramolecular Structure and Cellular Biochemistry 16 pp 243–258 (1981).

FIG. 4 is an alternative form of FIG. 1 using a p-n junction rather than a Schottky barrier for the diode 11. As before a chemical 25 is held in a chamber 26. The chamber side walls are formed of $SiO_2$ 34; the top by a p+ Si layer 27 coated with an In glue layer 28; and the bottom by a p+ Si layer 29. A p-n junction 30 is formed between the p+ bottom 29 and an n region 31 of Si. ZnO 32 surrounds the n region and is itself enclosed by a Ti layer 33 which connects with the In glue 28. A cermet layer or discontinuous metal film layer 35 is deposited to provide a resistive link between the n-silicon and the titanium layer 33. Processing steps are similar to that for the device of FIG. 1.

When illuminated with ultrasound, an a.c. voltage is generated in the piezo electric which drives a current up to the indium 28, through the chemical and the diode formed by 25, 30 and the resistor 35. The effect of the diode is to ensure that d.c. flow flow can only occur this way round. Hydrogen is evolved at the p+ cathode 29 and at the anode 27 the indium glue 28 is dissolved. The combination of these two effects lead to rupture of the cell.

The device of FIGS. 1 and 4 leak the electrolysing current through the zinc oxide 7 or resistor 14. A leakage path may instead be provided through a Schottky diode as explained with reference to FIGS. 6, 7.

Figure 5:
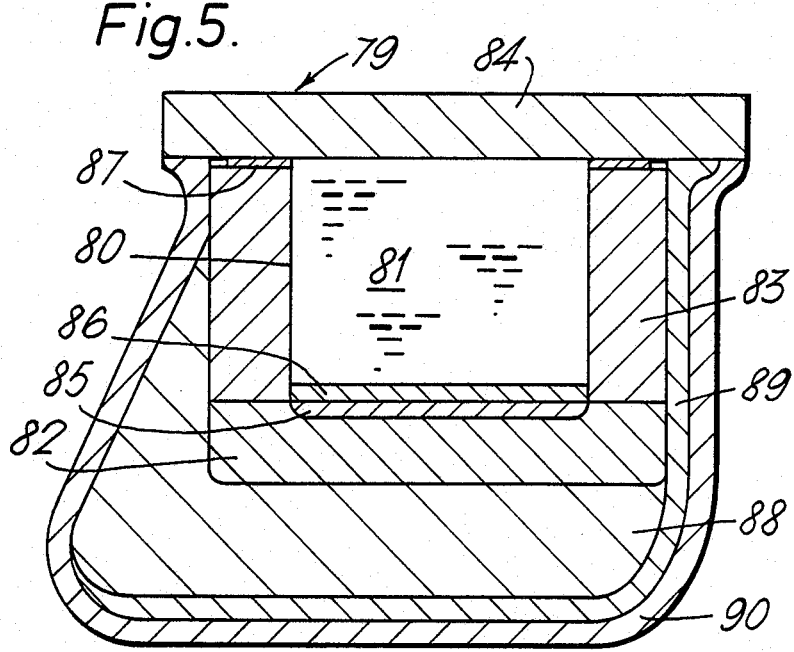
FIG. 5 is an alternative form of the device of FIG. 1.

As seen in FIG. 5 a device 79 for releasing chemical 81 in response to an acoustic signal comprises a closed chamber 80 formed of a bottom plate 82, silicon oxide walls 83, and a top plate 84. The bottom plate 82 is of n type silicon with an n+ region 85 in its upper surface. A thin layer 86 of Pt covers the bottom of the chamber. The top plate 84 is p type silicon fixed to the walls with indium glue 87. A layer 88 of piezo electric ZnO covers the bottom plate 82 and part of the side wall 83. This ZnO 87 is partly enclosed by a layer of titanium 89 which makes electrical contact with the top plate 84 and bottom plate 88 but not to the indium 87 and is itself enclosed by a passivating layer 90 of silicon dioxide.

Figure 6:
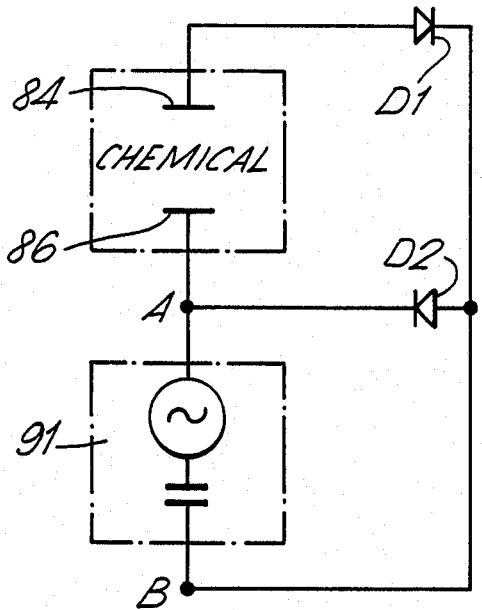
FIG. 6 is a circuit diagram for the device of FIG. 5.

FIG. 6 shows the circuit of the device of FIG. 5. A generating source 91 of electricity is produced across the ZnO layer 88 when illuminated by an acoustic beam. Diode D1 is formed by Schottky contact between Ti layer 89 and top plate 84, and diode D2 is formed between Ti layer 89 and the bottom plate 82.

When point A becomes negative with respect to point B current flows through diode D2. When point A becomes positive, with respect to B, then current flows through the chemical 81 and diode D1. The chemical electrolyses as before and is released from the chamber. Since silicon will form an anodic oxide on the passage of current in many solutions the bottom plate, which forms an anode, is covered with the Pt layer with the heavily doped n+ layer providing a contact.

The device of FIG. 5 may be formed by the following steps as shown in FIGS. 7.1 to 7.4:

1. Produce a silicon wafer 92 the bulk of which is lightly doped, with a very heavily doped (of the order of $10^{19}$ cm$^{-3}$) p-type layer 93 (typically 1 micron thick) covered with a lightly doped (about $10^{15}$ cm$^{-3}$) n-type layer 82 typically 0.5 microns thick. These can be produced by implanting a large dose of boron into p-type silicon 91, annealing, and growing an n-type epitaxial layer on the p+ layer 92.

2. Deposit a layer typically 2 microns thick of silicon dioxide 83 e.g. by chemical vapour deposition, evaporation, or sputtering.

3. Deposit a 400 nm layer of polycrystalline silicon 94.

4. Photolith and etch polycrystalline silicon 94 with a plasma.

5. Grow 400 Å of oxide 95 on the polycrystalline silicon 94. This will help to protect layer 94 in step 7 and densifies the oxide 83.

6. Photolith to produce a resist mask 96 outlining the devices.

7. Plasma etch the oxide 83 down to the silicon layer 82 using the resist mask 96. The resulting structure is shown in FIG. 7.1 with spaces separating devices.

8. Remove resist 96.

9. Etch n type silicon 82 using the oxide 83, 95 as a mask, going down to the p+ layer 93. This can be done using an alkaline wet etch such as 33% potassium hydroxide in water or EDP which will stop automatically when it reached the p+ layer. Alternatively a plasma can be used, but it in this case the resist 96 must be kept until this is done.

10. Plasma etch silicon dioxide 83 down to silicon layer 82. using the polycrystalline silicon 94 as a mask, see FIG. 7.2. This forms side walls to the chamber 80.

11. Remove the polycrystalline silicon 94 with an alkaline etch, a plasma, or by ion beam milling.

12. Implant arsenic and anneal to produce a shallow heavily doped n-type region 85 in the surface of the wafer 82.

13. Evaporate a layer 86 200 Å thick of platinum directly downwards. This will form the lower electrolysis electrode.

14. Use angled ion beam milling to remove platinum from the top of the oxide 83 while leaving it in the bottoms of the chambers 80.

15. The top surface of the silicon dioxide is covered with a thin layer of glue 87 for example by evaporation or printing. Suitable glues are indium evaporated onto the oxide, an epoxy resin or a rubber adhesive printed onto the oxide.

16. An upper waver is prepared from a p type substrate 97 carrying a 1 μm thick p+ layer 98 covered by a 0.5 μm thick p-type layer 84. Preparation is similar to step 1.

17. A chemical 81 is deposited in each device chamber 80 and sealed in by sticking the upper wafer down on to the lower one by the techniques described earlier.

18. The lightly doped substrate 92 of the original wafer is removed up to the p+ etch stop by means of an alkaline etch e.g. EDP or a mixture of potassium hydroxide, ethanol and water.

19. The p+ layer 92 is removed preferably by plasma etching. An etch consisting of 1 part of hydrofluoric acid, 3 parts of nitric acid and 8 parts of acetic acid, which will remove heavily doped but not lightly doped silicon, may also be used.

20. If indium solder is used as a glue 87 it is etched back slightly using a dilute acid.

21. Piezo electric material 88 e.g. zinc oxide is deposited by evaporating onto the exposed n-type silicon 82. The deposition is conducted at an angle so that some of the n-type silicon 82 is not covered.

22. A metal 89 is deposited which makes Schottky diodes onto both n-type and p-type silicon e.g. titanium, tungsten, nickel, or chromium. This may be done by angled evaporation inclined to the opposite side to that used for step 21. This metal must make contact to both the p-type silicon 84 on top of the device and to the n-type silicon 82 at the bottom of the device, and cover the piezoelectric layer 88.

23. A passivating layer 90 of silicon nitride, alumina or silicon dioxide is deposited over the metal 89 and the zinc oxide 88. This may be achieved by angled electron beam evaporation.

24. The p-type layer 84 between devices is etched through e.g. by means of a plasma or alkaline etch similar to those described earlier.

25. The devices are supported by a wax or polymer e.g. Apiezon W40 wax which covers the wafer and sticks it to a rigid support e.g. another wafer whose surface is passivated with silicon nitride.

26. The substrate 97 is removed by a selective etch which stops at the p+ layer 98. This may be achieved using EDP or mixtures of water, potassium hydroxide and ethanol.

27. The p+ layer 98 is removed, either by plasma etching, or by using a mixture of 1:3:8 hydrofluoric acid:nitric acid:acetic acid. This separates the devices which continue to be held by the wax.

28. The wax or polymeric support is dissolved, releasing the devices 79 which can be filtered out, and washed.

29. Antibody coatings can be applied if desired, and the devices can be suspended in saline for injection.

A variant on the process is to omit steps 25 and 26, and remove the p+ layer 98 with the 1:3:8 hydrofluoric acid:nitric acid:acetic acid etch by etching from below and filtering out the devices. In this case it is desirable that the passivating layer 90 deposited in step 23 should be of silicon nitride since it is attacked much more slowly than silicon dioxide or heavily doped silicon by the etch. Further variants involve replacing the p+ etch stop layers 98 by silicon dioxide layers. Buried silicon dioxide layers can be produced by high dose high energy ion implantation by recrystallising polycrystalline silicon on top of silicon dioxide (see S. M. Sze, VLSI Technology. McGraw Hill 1983 p 83 ff), or by anodising a p-type layer of silicon under a surface layer of n type material to form a buried layer of porous silicon which can be readily oxidised to give a buried oxide layer (K. Imai, H. Unns, I.E.E.E. Trans. Electron Devices, ED 31 (3) March 1984 p 297 ff, U.S. Pat. No. 3,919,060 H B Pogge et al 1974). A general review of methods of growing producing silicon on silicon dioxide is given by L. Jastrzebski, J. Crystal Growth 70 (1984) p 253–170.

FIG. 8 is an alternative to FIG. 6. As before device 100 comprises a chamber 101 formed by a p-type silicon bottom plate 102, silicon dioxide side walls 103, and an n type silicon top plate 104. A ring of indium glue 105 holds the top plate 104 in place. To avoid a Schottky barrier at the glue joint a thin n+ silicon layer 106 is formed on the lower surface of the top plate 104. A piezo electric layer 107 of ZnO is formed on the bottom plate 102 and part of the side walls 103. A layer of Ti 108 covers part of the ZnO layer 107 and makes electrical contact with the top plate 104. Contact by the layer 108 with the glue 105 is avoided by recessing the glue layer 105. A passivating layer 109 of silicon dioxide covers the ZnO and Ti layers 107, 108.

The device of FIG. 8 differs from that of FIG. 5 in that the top plate 104 acts as an anode and the bottom plate 102 as a cathode. Diodes are formed, as before, between the Ti layer 108 and bottom plate 102 and Ti layer 108 and top plate 104.

When a current flows gas is generated at the cathode 102. At the top plate anode 104 the silicon passivates through anodic oxide formation and the current then flows through the indium resulting in anodic dissolution of the indium glue 105. This provides both a build up of gas pressure and a dissolution of the indium glue. These two effects together lead to rupture of the device and release of chemical 110 in the chamber 101.

The process for making the device of FIG. 8 is similar to that for making FIG. 5 except that the lower substrate is p type and the epitaxial layer on the upper wafer is n type with a thin n+ layer on it. In step 20 the exposed area of this n+ layer is removed e.g. with potassium hydroxide etch, so the metal 8 makes contact to n silicon and not to the n+ layer, while the contact to the indium is made via an n+ layer so an ohmic contact is formed there.

Figure 9:
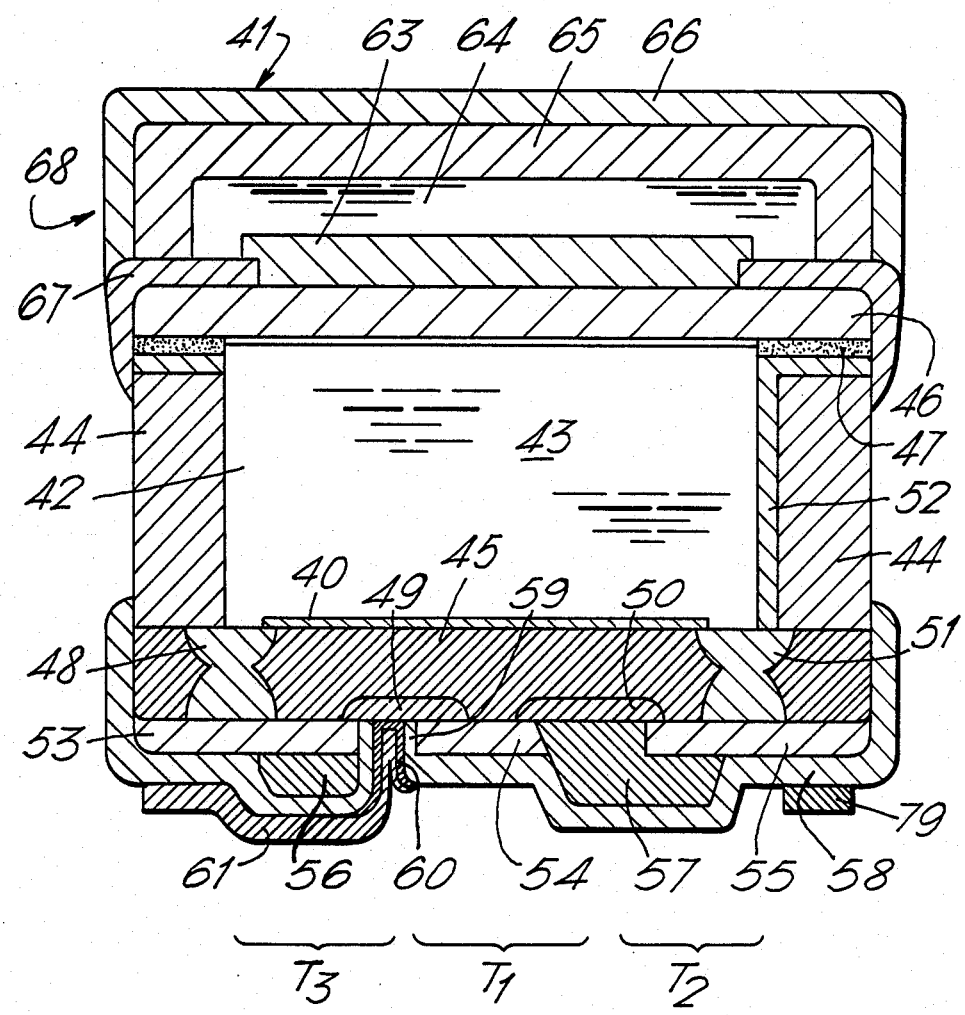
FIG. 9 is a sectional view of a device carrying a chemical, with a self contained battery and signal processing circuit.

A self contained and self powered device 41 is shown in FIG. 9 with its circuit diagram in FIG. 10. It comprises a chamber 42 containing a chemical 43 such as a nitrogen mustard. The chamber walls 44 are formed of $SiO_2$, the base 45 of p-type Si and the top 46 or p+ Si. A layer 47 of indium holds the top to the walls. The bulk of the base 45 is electrically isolated from the chemical 45 by an oxide layer 40.

Below the chamber 42 is a processing circuit formed by four Field Effect Transistors (FET) devices T2, T3, T4, T5 and a chemically sensitive FET (CHEMFET) T1. The transistors T4 and T5 are not visible in the cross section shown in FIG. 5. In the bottom plate in FIG. 9 are four diffused regions 48, 49, 50, 51, with a metal strip 52 connecting the region 51 with the top plate 46. A layer of $SiO_2$ forms gate insulators 53, 54, 55. Gate electrodes 56, 57 are formed by deposited Al, gate 57 is also connected to the gate of T5 and gate 56 is connected to the output of an inverter formed by T4 and T5. A layer 58 of $Si_3N_4$ covers the gate electrodes 56, 57 and oxides 53, 54, 55, with a hole 59 to the n+ diffusion 49. This hole 59 is covered with a layer of refractory metal 60 forming both a conductor and diffusion barrier. A layer of Ag 61 covers the metal 60 and gate electrodes 56, 57 to form a switch terminal 62. Since silver has a large work function and is also connected to the most negative point in the circuit, the silicon beneath it will tend to invert. Thus silver on the surface 79 can be used to supplement or avoid the need for channel stop implants to isolate the transistors.

Above the chamber 42 is a battery 68 formed by a bottom electrode 63, electrolyte 64, top electrode 65 and Ag switch terminal 66 in serial layer order. An insulating alumina ring 67 is arranged on top of the p+ top plate 46 and extends below the indium glue 47 onto the side walls 44.

FIG. 10 shows the circuit diagram for the device of FIG. 9. The battery 68 is formed by the negative electrode 65, electrolyte 64, and positive electrode 63. The Ag layer 66 forms one terminal 69 of a switch 70, with the lower Ag layer 61 forming the other switch terminal 62. Immersion of the device 41 in a suitable solution, e.g. blood, completes the circuit between the two terminals 62, 69. When kept under dry conditions the two terminals 62, 69 are unconnected and so the battery 68 does not run down.

Transistor T3 is formed by the n+ regions 49, 48 acting as source and drain respectively; gate insulation is provided by the oxide 53 and the gate electrode provided by the Al region 56.

Transistor T2 is formed by the n+ region 50 forming a source; the n+ region 51 acts as a drain; oxide 55 forms the gate insulation; and Al region 57 forms a gate electrode and is connected to the source.

The CHEMFET T1 has a source formed by n+ region 49 and drain formed by n+ region 50; oxide 54 forms the gate insulation. As seen in FIG. 9 there is no gate electrode. In a CHEMFET a gate voltage appears at the nitride surface 58 due to the pH value of the solution in which the device is immersed. Thus the source drain current is a measure of the pH at the nitride/solution interface.

Details of CHEMFETs are given in:

Ion Selective Electrodes in Analytical Chemistry Vol. 2, Editor H Freise, Plenum Press NY 1980 article by J Janta and R J Huber, P 107-173 Chemically Sensitive Field Effect Transistors.

Figure 13:
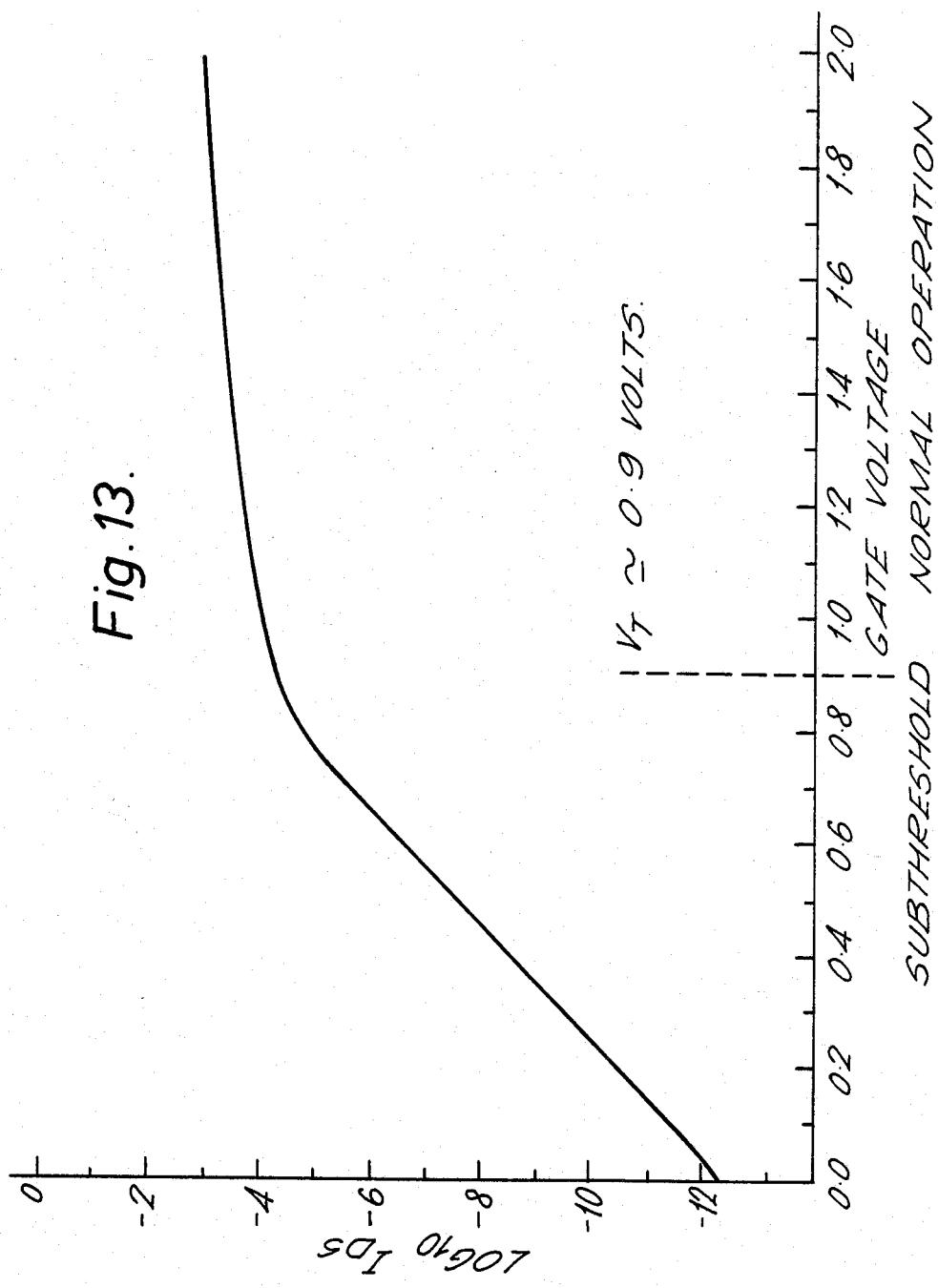
FIG. 13 is a graph of current against voltage for an FET.

The device transistors T1 and T2 and T3 operate in what is termed the sub-threshold mode. FIG. 13 shows the voltage-current curve for a field effect transistor (FET). Normally such a device is operated with a gate voltage above a threshold value shown as $V_T$. Below $V_T$ the current consumption is very small but large changes occur with voltage. Sub-threshold mode operation is described for example in:

M oB Barron—"Low Level Currents in Insulated Gate Field Effect Transistors", Solid State Electronics, Vol. 15 (1972) p. 293

R. M. S. Sanson & J. D. Meingl—"Ion Implanted Complementary MOS Transistors in Low Voltage Circuits", I.E.E.E. Journal of Solid-state Circuits SC-7 No. 2 (1972) p. 146

R. J. VanOverstraeten et al—"The Influence of Surface Potential Fluctuation on the Operation of the MOS Transistor in Weak Inversion", I.E.E.E. Transactions of Electron Devices, ED-20 No. 12 (1973) p. 1154

R. J. VanOverstraeten et al—"Inadequacy of the Classical Theory of the MOS Transistor Operating in Weak Inversion", I.E.E.E. Transactions on Electron Devices, ED-20 No. 12 (1973) p. 1150

R. R. Troutman—"Subthreshold Design Consideration for Insulated Gate Field-Effect Transistors", I.E.E.E. Journal of Solid-State Circuits, SC-9 No. 2 (1974) p. 55

R. R. Troutman—"Subthreshold Slope for Insulated Gate Field-Effect Transistors", I.E.E.E. Transaction on Electron Devices (1978) p. 1049

R. W. J. Barker—"Small Signal Subthreshold Model for I.G.F.E.T.S.", Electronic Letters, Vol. 12 No. 10 (1976) p. 260

E. Vittoz & J. Fellrath—"CMOS Analog Integrated Circuits based on Weak Inversion Operation", I.E.E.E. Journal of Solid-state Circuits, SC-12 No. 3 (1977) p. 224

P. Antognetti et al—"CAD Model for Threshold and Subthreshold Conduction in MOSFETS", I.E.E.E. Journal of Solid-state Circuits, SC-17 No. 3 (1982) p. 454.

The gate voltage of a nitride pH detecting CHEMFET changes by about 55 mV per pH unit. A change in 1 pH unit will therefore change the resistance of an FET, operating in the sub-threshold mode, by a factor of more than 3.5. This changes the voltage on the T5 gate from about 65% to 35% of the battery voltage. For a 3 volt battery this is a change of 0.9 volts which is sufficient to turn T5 on or off. Changes in pH of about 0.5 units will switch T5. T5 and T4 form an inverting switch so when T5 is turned off, the gate voltage to T3 rises and T3 turns on.

In use about $10^8$ devices of FIG. 9 are mixed into about 10 cc of saline solution and injected into a suitable blood vessel. Normal blood flow circulates these devices within the vascular system. The blood pH varies within the body, around a tumour it may drop by around 0.4 units. For a large intraperitoneal injection of glucose this differences increases to one pH unit as described by:

M. Eden, B. Haines, H. Kahler, J. Nat. Cancer Inst., 16 (2) p. 541 ff (1955)

H. Kahler, W. V. B. Robertson, J. Nat. Cancer Inst., 3, pp. 495–501 (1943)

P. Gullin et al, J. Nat. Cancer Inst., 34 (6) p. 857 ff (1965)

S. A. Shah, R K. Jars, P. L. Finney, A. L. Yee, 35th Annual Conference on Engineering in Medicine and Biology, Marriott Hotel, Philadelphia, PA, Sept. 22-24, 1982, p. 138.

When in the blood the battery is switched on since blood conducts electricity. The battery voltage is divided between the CHEMFET T1 and FET T2 acting as a resistor because its gate and source are connected together, both operate in sub-threshold mode and so consume very little power. If the blood pH falls, the drain voltage of T1 changes and comparatively large changes are produced in the gate voltage of T5 thus turning it OFF. This causes the gate voltage of T3 to rise turning it on.

In this condition the battery 68 is connected across the chemical chamber 42, i.e. between p+ plate 46 and n+ region 48, so the chemical 43 is electrolysed. The resulting gas pressure ruptures the chamber 42 and releases the chemical 43 into the blood at the position of low pH.

Processing steps to produce the device of FIG. 9 are shown in FIGS. 11.1 to 11.8.

1. A p-type layer 45 0.5 $\mu$m thick is formed on a p+ silicon substrate 75. The p+ substrate may extend for the whole thickness of the wafer or may itself be a thin layer on a lightly doped wafer. Typically the p-type 45 layer has resistivity greater than 0.06 ohm cm and the p+ substrate 75 is less than 0.01 ohm cm.

2. Clean the p-layer 45 and deposit $SiO_2$ 1.5 $\mu$m thick 44.

3. Use photo lithography and a plasma etch to produce chamber walls 44, FIG. 11.1. Typically the walls 44 are 0.5 $\mu$m thick with an internal diameter of 1.5 $\mu$m.

4. Grow a 1000 Å thermal oxide layer 40.

5. Ion beam mill or reactive beam etch with the beam incident at an angle to make 2 holes 38, 39 in the oxide layer 40.

6. Form n+ regions 48, 51 in the base 45 by implanting phosphorous through the holes 38, 39. Implanting $5 \times 10^{15}$ cm$^{-3}$ of phosphorus at 30 keV allows the 1000 Å oxide 40 to act as a mask, FIG. 11.1.

7. Evaporate a refractory metal 52, at an angle to provide a strip 52 connecting the n+ region 51 with the top of the chamber 42, FIG. 11.2. Platinum is preferred. This will also act as an additional region of anode for electrolysing the chemical. This is desirable since silicon tends to form an anodic oxide in many electrolytes.

8. Coat the whole of upper side of the substrate with a refractory non-contaminating inorganic oxide 76. One possible support is magnesium oxide. An alternative is to deposit 1800 Å of chemical vapour deposited silicon nitride followed by 250 $\mu$m of polycrystalline silicon. Processes for the deposition of thick polycrystalline layers have been developed for bipolar SOI applications (see L. Jastrzebski, J. Crystal Growth 70 (1984) p. 253–270). This oxide 76 acts as a support for subsequent processing so a thick layer is required.

9. Etch away the p+ material 75 of the original substrate. A suitable etchant is 1 part HF (aq.):3 parts HNO$_3$ (aq.):8 parts CH$_3$COOH. This removes p+ but not p-type Si 45.

10. Form four n+ regions 48a, 49, 50, 51a by implanting phosphorus or arsenic through a resist mask and annealing. Two of the n+ regions 48a, 51a connect through the p-layer 45 to the n+ regions 48, 51, inside the chamber 42. Threshold adjustment and channel stop implants can also be done at this stage as required using resist masking layers.

11. Grow a SiO$_2$ layer 0.15 $\mu$m thick 53, 54, 55.

12. Remove SiO$_2$ layer between separate devices.

13. Remove the p-type Si 45 between devices to separate them, FIG. 11.3. This is achieved using the oxide 53, 54, 55 as a mask and plasma etching or a chemical etch such as hydrazine water or ethylene diamine pyrocatechol water.

14. Open up holes in oxide layer to form connections with the n+ regions 49, 50 FIG. 7.3 for three transistors T1, T2, T3. At the same time the silicon dioxide 40 between the devices is etched through.

15. Form electrodes 56, 57 by depositing and etching a conducting layer of Al, a refractory metal, or polysilicon, FIG. 11.3. These electrodes form the gates of T2, T3, T4, T5 and connect the source of T2 to the gates of T2 and T5 and the source of T4 to the gates of T4 and T3.

16. Deposit an Si$_3$N$_4$ (nitride) layer 58 by a chemical vapour deposition (C.V.D.) or (if Al metalisation is used) a plasma assisted C.V.D. process. The nitride 58 covers the whole base of the device and extends up to overlap the chamber walls 44, FIG. 11.4.

17. Open up a hole 59 in the nitride 58 to the n+ region 49 using a resist mask and plasma etch. In this process nitride connecting the devices is removed, FIG. 11.4.

18. Deposit a conducting refractory metal, e.g. molybdenum or tantalum, as a diffusion barrier 60. This prevents diffusion of sodium into the oxide 53, 54, when the device is in use.

19. Deposit Ag 61.

20. Etch away Ag 61 and refractory metal 60 to leave them shaped as in FIG. 11.5 with exposed nitride 58 at the gate of the CHEMFET T1. A suitable etchant for silver is nitric acid or potassium cyanide. Alternatively ion beam milling with a resist mask can be used.

21. Apply hydrochloric acid to form a silver chloride layer on the silver electrode 61.

22. Coat bottom surfaces with a polymer or wax e.g. APIEZON W40 wax 77 applied molten and allowed to cool. Preferably this coating is thin (e.g. a few $\mu$m) and serves to stick the chips to a rigid support e.g. a silicon wafer or glass disc. This provides a support for later processing steps.

23. Remove inorganic support 76 from the top of the devices. A suitable etchant for MgO is hydrochloric acid. Polycrystalline silicon can be removed by potassium hydroxide solution or by mixture of hydrofluoro acid, nitric acid and acetic acid. A silicon nitride layer can be removed by a plasma or by hot phosphoric acid. The structure is shown in FIGS. 11.5, 11.6.

24. Deposit a thin e.g. 0.1 $\mu$m layer of indium 47 onto the top of the chamber 44 by evaporation at a shallow angle FIG. 11.7. This acts as a glue for the chamber top.

25. Fill chamber 42 with the desired chemical 43. Remove surplus by spinning or wiping with an absorber or on fixing chamber top as described earlier in the context of the piezo electric powered device.

26. Place a p-type Si wafer 78 with a 0.4 μm p+ layer 46 and a coating 0.05 μm of In 47 onto the chamber walls 44. Pressure of about $3 \times 10$ Nm$^{-2}$ and/or ultrasound e.g. at 20-60 kHz fixes the wafer 77 to the chamber walls FIG. 11.7. Typically the p+ layer 46 has a carrier concentration/doping level $2 \times 10^{20}$ cm$^{-3}$, FIG. 11.7.

27. Remove p-type Si 78 with a selective etch e.g. alcoholic KOH. This does not remove the p+ material 46.

28. Evaporate or sputter SiO$_2$ onto the p+ layer 46.

29. Using photolithography expose the p+ layer 46 over the gaps between the devices.

30. Etch p+ layer 46 to separate each device, FIG. 11.8.

31. Remove SiO$_2$ from p+ layer 46, e.g. by plasma etching, thereby avoiding damaging the oxide on the sides of the devices.

32. Evaporate or sputter Si$_3$N$_4$ or alumina 67 over the p+ layer and extend downwards onto the chamber walls 44 thus covering the indium 47 and refractory metal 52 with an insulator.

33. Form a hole in the nitride 67 to expose the p+ layer 46 FIG. 11.8 by photolithography. The nitride can be plasma etched.

34. Form a battery bottom electrode 63 by evaporation or sputtering. A suitable material is V$_6$O$_{13}$, or CoO$_2$ or V$_2$O$_5$/B$_2$O$_3$ with a typical thickness of 0.3 μm.

35. Form an electrolyte layer 64 typically 0.3 μm thick by evaporation or sputtering. Suitable materials are (LiPO$_3$)$_{0.67}$·(LiI)$_{0.33}$ glass; (LiS$_2$)$_{0.37}$·(P$_2$S$_5$)$_{0.18}$·(LiI)$_{0.43}$ glass. Alternatively polyethylene oxide doped with lithium chlorate (PEO)$_8$LiClO$_4$ could be applied by dip coating or spinning.

36. Form the negative electrode of the battery 65 by evaporation or sputtering. Suitable materials are Li or LiIn or LiAl typically 0.3 μm thick. This is followed by a refractory metal e.g. W, Mo, Ta which can be electron beam evaporated, and which prevent moisture from diffusing into the lithium.

37. Deposit Ag 66 by evaporation or sputtering.

38. Expose Ag to HCl to form AgCl electrode 66.

39. Dissolve black wax 77 or polymer support. The devices are now detached.

40. Wash and dry the devices and store in dry atmosphere. The devices are then ready for mixing into a saline solution when needed.

FIGS. 12.1 to 12.3 show an alternative fabrication process, which avoids the need for supporting the devices at intermediate high temperature stages and is suitable for devices containing circuits. This has the following steps:

1. Provide an Si substrate 114 with a layer of about 0.5 μm of silicon 116 on silicon dioxide 115. Pattern and etch the silicon 115 to produce islands of silicon 116 on silicon dioxide 115 and fabricate circuits 117, 118 in them. References to silicon on silicon dioxide technology are given above.

2. Passivate circuits 117, 118 and protect with a layer 119 of 2000 Å of evaporated silicon. Pattern this layer 119 where contact holes are going to be needed.

3. Deposit 2 μm of silicon dioxide 121 by chemical vapour deposition or evaporation or sputtering.

4. Photolith and plasma etch the oxide 121 back to the silicon 116 thus forming chamber walls.

5. Deposit 1000 Å of silicon nitride 122 by chemical vapour deposition or sputtering and plasma etch to remove it from nonvertical surfaces.

6. Use angled evaporation to produce contact 128 to the circuit from the top of the silicon dioxide.

7. Produce a top wafer consisting of a 0.3 μm p+ (approximately $2 \cdot 10^{20}$ cm$^{-3}$) layer 123 on a lightly doped substrate 124.

8. Deposit indium adhesive 125 on the top of the silicon dioxide 121 and/or on the top wafer p+ layer 123.

9. Coat with chemical payload 127 and push substrate 114, 124 together as described earlier to seal in chemical 126, FIG. 12.2.

10. Remove the lightly doped substrate 124 with a selective etch which does not attack the p+ layer 123 e.g. potassium hydroxide solution.

11. Evaporate or sputter a silicon dioxide layer over the whole p+ layer.

12. Photolith and etch to remove the silicon dioxide over the gaps between the devices.

13. Etch through the p+ layer 123 using the oxide from step 12 as a mask to separate the devices.

14. Fabricate and encapsulate a battery 127, FIG. 12.3 as in steps 29–36 in the previous process.

15. Etch in hydrofluoric acid to dissolve silicon dioxide layer 116 and separate devices. Wash and dry devices and store in a dry atmosphere.

Figure 14:
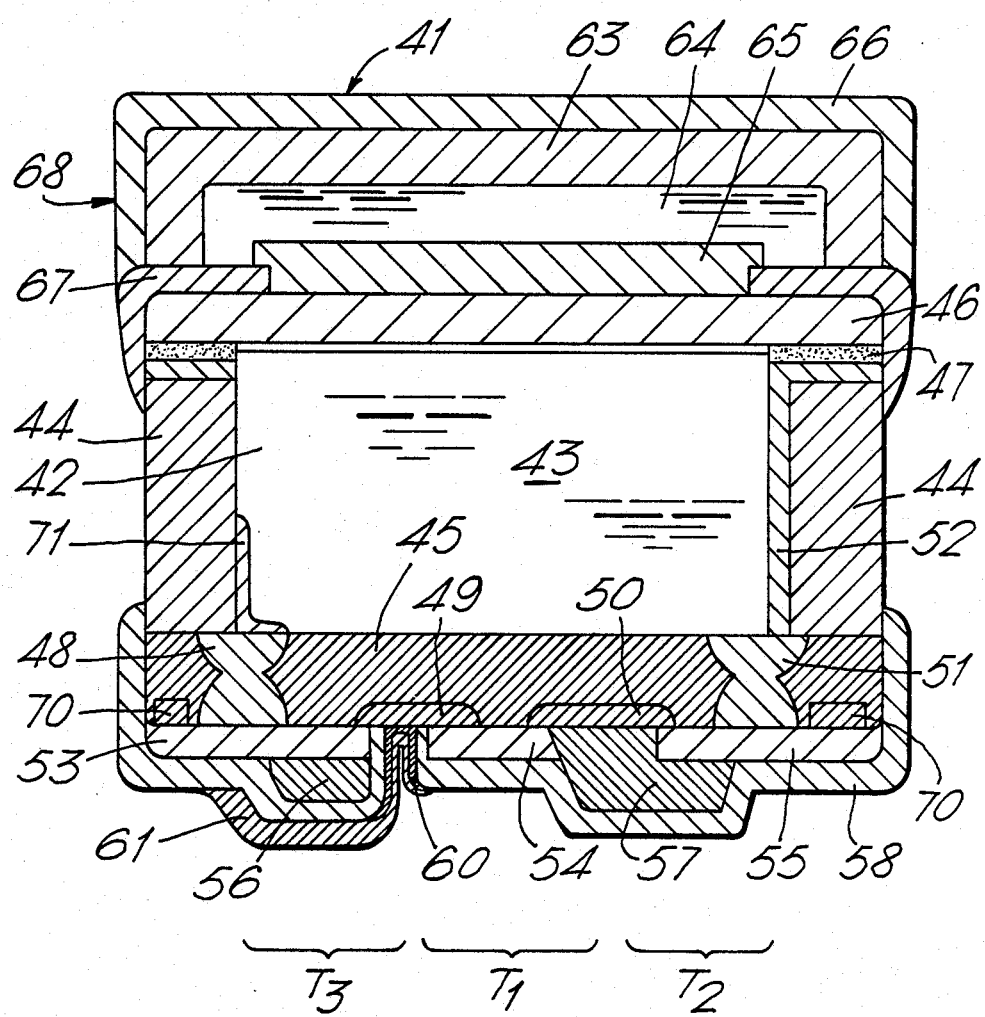
FIG. 14 is an alternative form of the device of FIG. 9.
Figure 15:
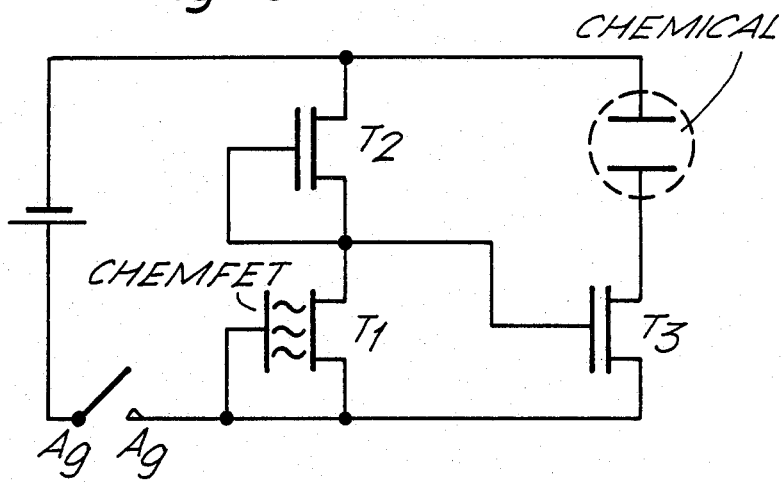
FIG. 15 is a circuit diagram of FIG. 14.

An alternative implementation of a similar device in PMOS is illustrated in FIGS. 14 and 15 and given the same reference numerals as FIGS. 9, 10. As the solution becomes more acidic, $V_T$ of a CHEMFET T1 becomes more negative and turns off. This causes a negative voltage to be applied to the gate of T3 which conducts causing a current to flow through the chemical which electrolyses leading to rupture of the cavity and release of the chemical. The mode of operation is the same as that of the NMOS device of FIG. 9 except that no inverter is required so two fewer transistors (T3, T4) are needed. The construction process is identical except that an n-type wafer and p-type implants are needed to make the device and n+ channel stops 70 are required to isolate the transistors. No oxide is needed to separate the bulk of the silicon from the solution but some platinum 71 needs to be deposited on the positive electrode and patterned to provide an electrolysing contact since a silicon contact might form an anodic oxide. The platinum can be deposited by angled evaporation and ion beam milling used to remove material from the upper parts and tops of the container walls.

Devices similar to those of FIG. 9 can be made to sense temperatures and discharge their chemical when a given temperature is reached. For example tumours are at a higher temperature than surrounding tissue. Thus drugs can be released at a tumour site.

To measure temperature diodes may be used instead of a CHEMFET. The reverse bias leakage of diodes exhibits very strong temperature dependence. For example in silicon the leakage approximately doubles for each 8° C. rise in temperature.

Figure 16:
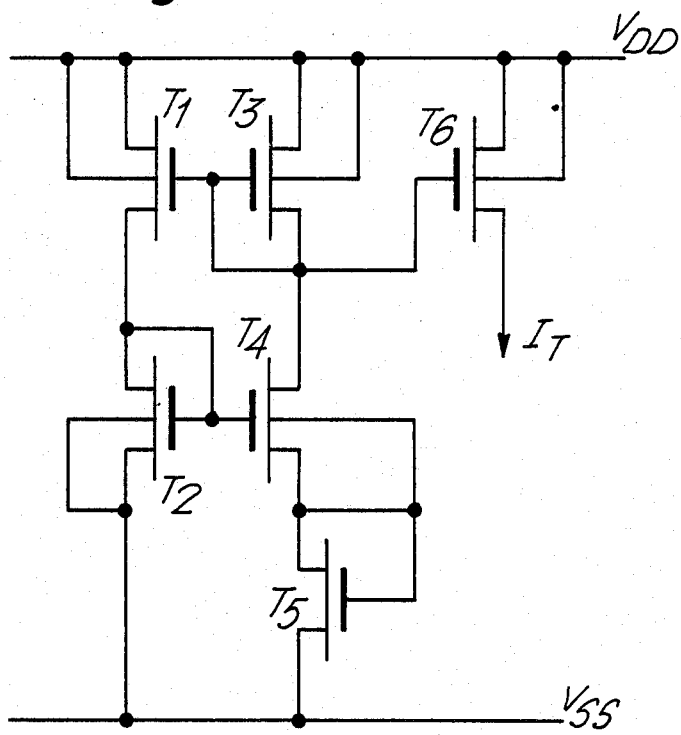
FIG. 16 is a circuit diagram for a temperature-current sensor.
Figure 17:
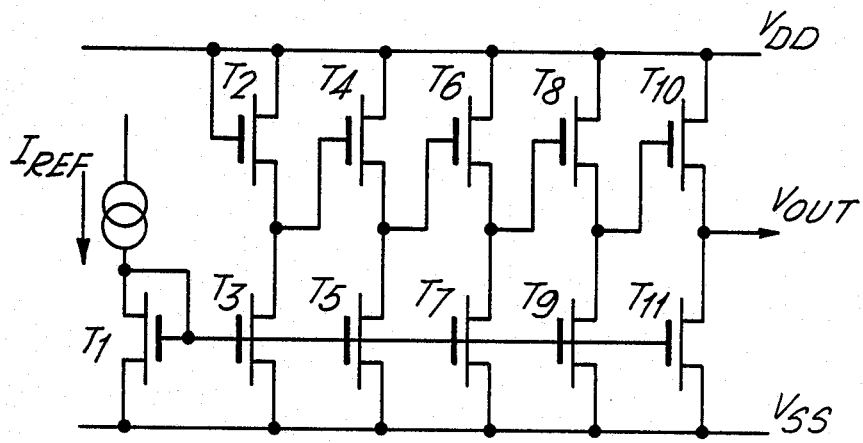
FIG. 17 is a circuit diagram for a temperature-voltage sensor.

Alternatively temperature can be measured by means of the temperature dependence of the subthreshold conductance employing circuits such as those illustrated in FIGS. 16 and 17. In the circuit of FIG. 16, the transistors T1-T4 set the gate voltage of T5 to $$\frac{N_n kT \log_e}{q} \left( \frac{S1 \cdot S4}{S2 \cdot S3} \right)$$

where
S=width/length of the channel of a given transistor.
Nn=Ideality factor describing the subthreshold slope of an n channel MOSFET equal to $$\frac{q}{kT} \frac{\log I_{DS}}{V_g}$$

T=Temperature
k=Boltzmanns constant
q=electronic charge.

The current through T5 and thus the current through T3 therefore rises exponentially with temperature. Since the drain and gate of T3 are linked, the drain voltage of T3 is therefore linearly dependent on temperature. The transistor T6 forms a current mirror from T3 so $I_T$ increases exponentially with temperature. In the circuit of FIG. 12, the gate voltage of T1 rises linearly with temperature. Transistors T3, T5, T7, T9 and T11 are current mirrors. The pairs of transistors T2, T3; T4, T5, etc form source followers, and the source voltage of each one is equal to its gate voltage plus a constant which varies linearly with temperature so $V_{out}$ is roughly half way between the rails $V_{DD}$ and $V_{SS}$ and varies linearly with temperature.

As before the device may be partially coated with an antibody or with an enzyme. An enzyme may react with a specific substrate to change the local pH which may be detected by a CHEMFET, thus increasing the range of materials which the same silicon structure can respond to.

Alternatively, the device may be encapsulated in a cell, e.g. a white cell. This may be achieved by allowing white cells to engulf the device in vitro and to inject the resultant white cells and devices. Since the body sees the white cells as friendly the devices are not trapped.

Figure 18:
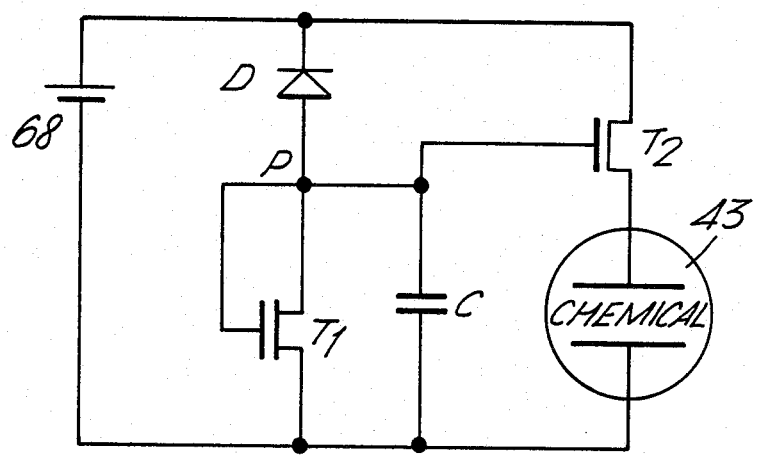
FIG. 18 is a circuit diagram for a device carrying a chemical to be released on receipt of ionising radiation.

FIG. 18 is a circuit diagram for a device similar to FIG. 9 but which releases a chemical 43 in the presence of ionising radiation. The device includes a battery 68, diode D, capacitor C and FET T1, T2 as before. The transistor T1 only passes a very small current. When an ionising event e.g. the passage of an alpha or beta particle occurs in the diode D, the current flows in the diode. This raises the potential of point P, charges up the capacitor C and turns T2 on. Current flows through T2 and into the chemical which it releases by electrolyte rupture in the usual manner. The device is used in conjunction with a radio labelled antibody. First the target tissue e.g. the tumour is labelled using a radio labelled antibody. The isotope should emit alpha or beta particles. The devices are then introduced into the bloodstream. This allows the targets to be attacked simultaneously with both radiation and chemical agents.

A further example of this invention uses devices that are comparatively long e.g. up to 500 μm. These cannot circulate through capillaries but can pass along larger blood vessels. Thus by choosing device size and point of injection into the body devices can be carried deep into selected organs where whey will lodge. Providing the shape is arranged not to block blood vessels the devices may relatively safely remain in the vessels and perform their required task. Suitable device shapes are L-shape and cross-shape.

These larger devices can cary relatively complicated processing circuits for sensing a required parrameter, e.g. temperature or pH, and provide an output signal for exernal detection or a slow release of drugs on command.

Figure 19:
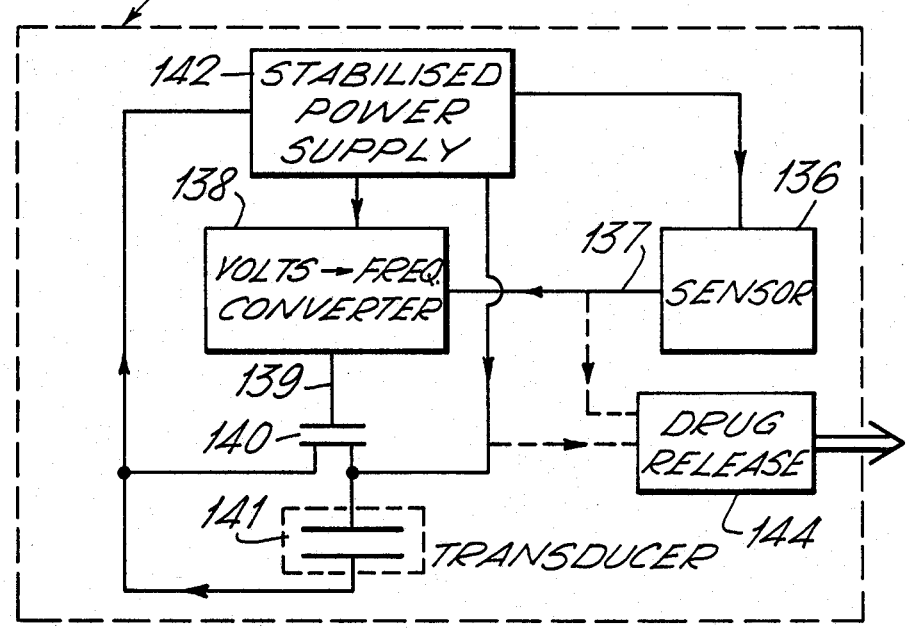
FIGS. 19, 20 are circuit diagrams for devices larger than those of FIG. 14 for lodging in selected organs.

An example of a circuit for use in these larger devices is shown in FIG. 19. The device is formed as an integrated device 135 in the same manner as in FIG. 1 or 14. A sensor 136 of temperature or pH provides a variable voltage signal 137 to a voltage to frequency converter 138 e.g. a voltage controlled oscillator. Output 139 from this converter modulates a signal flowing through an FET 140 from a transducer 141. This transducer 141 may be a layer of piezo electric material between two electrically conducting plates. The plate may be of dipole dimensions. When irradiated by a sound source the transducer 141 provides a voltage signal at the source frequency. A stabilised power supply 142 takes an input from the transducer 141 to power the converter 138 and sensor 136. Modulation of the signal passing through the transducer 141 and F.E.T. 140, representing sensor output, is detected externally e.g. by circuits similar to those used for detecting doppler shifted radar returns. Conditions within a patient's organ under a study can therefore be monitored continuously.

Figure 20:
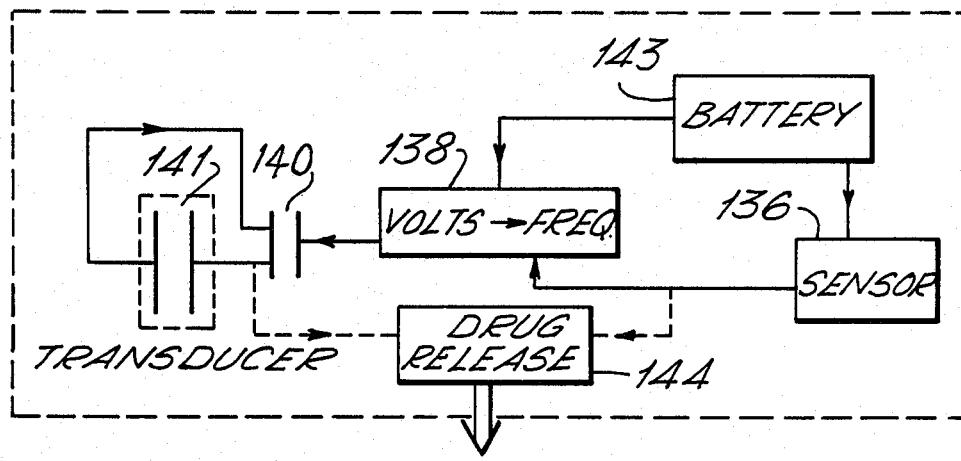

The circuit of FIG. 20 is similar to that of FIG. 19. It has a sensor 136, voltage to frequency converter 138 and sensor 136. Instead of power being taken from an external source the device contains its own battery 143. As in FIG. 19 the transducer and F.E.T. 140 provide a modulated signal when irradiated by a sound source.

Instead of or in addition to transmitting information the device of FIGS. 19, 20 may release drugs 144. Under the control of the sensor 136 output or under the control of the externally applied sound signal. Such drug release may be achieved by gas pressure generated by electrolysis and may be over a prolonged period continuously or intermittently.

More than one drug may be carried independently in the same device and released together or in sequence.

The sensor 136 may be sensitive to ionising radiation, e.g. X-rays or alpha particles. Thus when an organ is irradiated by alpha particles or X-rays a drug would be released to reinforce the radiation treatment. Alternatively the sensors 136 may be sensitive to radio frequency signals to release drugs on command.

For devices such as those in FIG. 1 designed to circulate within an animal blood circulation system it is necessary to know:
(i) how long devices stay in the blood:
(ii) how they are removed:
(iii) whether any major adverse effects are produced by the devices.

To provide these results solid silicon microdiscs were neutron activated, mixed into a saline solution, and injected into a pig's blood vessel. Blood samples were taken at regular intervals and the radioactivity of the blood measured. This showed how long the microdiscs stayed in the blood circulatory system. After blood sample measurements indicated nearly all the microdiscs had been removed from the blood the pig was killed. The radioactivity of various tissues were measured to determine where the microdiscs had finally lodged. Sections of tissue were prepared for histological examination to see if there was any grouping together of microdiscs and to determine the microvascular site of trapping.

Three experiments was performed, the design of each experiment being largely dictated by the results of the previous one. Discussion prior to the first experiment had concluded that microdiscs having a long clearance half life in blood would offer greater clinical usefulness and that the first experiment should assess the clearance rate and trapping sites of very small microdiscs, smaller than red blood cells, which could reasonably be expected to remain in circulation for long periods (hours). The microdiscs were however large enough to carry a useful electronic circuit and drug payload. All experiments were performed with polycrystalline silicon microdiscs labelled with arsenic 76 (a gamma emitter). The discs did not contain circuits or drug payloads.

Experiment 1 was performed with three micron square microdiscs which were 700 nm thick. These microdiscs were cleared from the blood extremely quickly following intravenous administration; the vast majority were trapped in the lungs on either the first or second circulation of the microdiscs. The extremely rapid clearance was ascribed at the time to the square shape and sharp corners of the microdiscs.

Experiment 2 used 3 micron diameter circular microdiscs with a lower specific activity of arsenic 76. Clearance was nearly as rapid as with the 3 micron square microdiscs, resulting in barely detected levels of radioactivity in the blood at the time of the first blood sample which was taken after 2 minutes. These clearance rates were extremely surprising. Pulmonary capillaries are reported to be seven to nine microns in diameter. The high clearance rates suggest that mechanical trapping may not be the sole mechanism responsible for the pulmonary accumulation of microdiscs.

Experiment 3 used 1.5 micron circular microdiscs in an attempt to reduce the rate of mechanical entraplment of the microdiscs. Clearance rates were even higher than for the 3 micron circular discs. Experiments were then suspended to review progress and to identify further avenues of experiment.

Procedure

Pigs of a Large White strain were sedated with an air/halothane mixture and aneasthetised with sodium pentobarbitone. Pigs were tracheotomised and allowed to breathe spontaneously. The femoral artery and vein of one leg were exposed and cannulae passed into the abdominal aorta and inferior vena cava. The pig was placed in a dorsal recumbent position and maintained by bolus intravenous administration of sodium pentabarbitone as required. Table 1 presents details of the specific activities of the microdiscs. The microdiscs were suspended in 2 ml of 0.9% saline by ultrasonification. Eighty percent of the solution was extracted for experiments 1 and 2 (93% for experiment 3) and made up to 5 ml with 0.9% saline. Small aliquots (either 10 microliters or 25 microliters) were withdrawn as standards to estimate the total activity ultimately injected into the animal and to provide a check on the half life of the radio isotope. Arsenic 76 should be the predominate isotope with a half life of 26.3 hours.

The microdiscs were administered intravenously over 1 minute with multiple rinsing of the catheter and stock solution syringe. Blood samples were withdrawn intra arterially at two minute intervals for Experiments 1 and 2 and initially at one minute intervals in Experiment 3. One milliliter of each sample of withdrawn blood was centrifuged and radio activity measured in a Wilj Model 2001 gamma Counter. At the end of the blood sampling period the animal was killed by exsangrination whilst still under the influence of anaesthetic and then subjected to a post mortem examination. Samples of tissues of 0.5–1 gramme were taken, weighed and the radioactivity measured. A total of 15 samples were taken for Experiment 1, 22 for Experiment 2 and 60 for Experiment 3. Further samples of lung were taken for histological examination to assess the site of trapping and whether agglomeration of the microspheres had occurred. All measured radio activities of the standards, blood and tissue samples were corrected for decay to a common time.

Results

The entrapment of the microdiscs was so efficient for the 3.0 micron square and circular discs that the measured activity within the blood was barely above background even though 720,000 cps and 300,000 cps respectively had been administered intravenously (Table 1). Table 2 shows measured activities expressed as cps/ml whole blood for these discs. In the light of these observations the 1.5 micron microdiscs were prepared with a substantially greater arsenic 76 activity and were administered into a pig of lower body mass (Table 1). Significant entrapment of the 1.5 micron particles in the first minute still occurred (Table 2) but measured activities in the blood still showed a three fold increase above background, even after 60 minutes.

Table 4 shows isotope activity in the blood expressed as a fraction of projected blood activity assuming instantaneous and uniform mixing of the microdiscs within the projected blood volume. The projected activities were 249 cps/ml, and 2,464 cps/ml for Experiments 1, 2 and 3 respectively (Table 1). An extremely large proportion of the injected microdiscs were cleared prior to the first blood sample at 2 minutes. Approximately 98% of the 3 micron squares, and 95% of the 3 micron circles were trapped by this time. The fraction of the microdiscs remaining in the blood which were trapped in the next 28 minutes was quite low. The high specific activity of the 1.5 micron circular microdiscs administered in Experiment 3 permitted a more accurate estimate of the clearance rate in this case. Table 3 shows that after one minute, only 0.95% of the administered microdiscs remained in circulation. Further entrapment occurred over the ensuing minutes and after 59 minutes only 0.24% of the administered microdiscs were still circulating. The relative blood activity as a fraction of time is shown in graphical format in FIG. 7.

In all three experiments the majority of the microdiscs were trapped within the lung following intravenous administration. The isotope activity expressed as cps/g wet weight of tissue are presented in Table 4. Table 5 shows the same data expressed as tissue activity divided by the level of activity which would have occurred if the injected activity were spread uniformly through the body with a constant level of activity per unit mass of tissue. In Experiments 1 and 2 (3 micron microdiscs) notable quantities of microdiscs crossed the pulmonary vasculature and could be detected in, as expected, those organs receiving a significant blood flow per gramme of tissue, namely the liver, kidney and spleen. Activity could also be detected in samples of pancreas, heart, bowel, brain and skeletal muscle—the activity in these organs was very low being only approximately double the background level. The 1.5 micron microdiscs injected in Experiment 3 showed the same general pattern of distribution. The vast majority of the microdiscs were again trapped in the lung with the "relative activities" of the samples extending over a large range of 13.0 to 199.9; the mean ± standard deviation "relative activity" of the 28 lung samples being 113.2±53.8. A small proportion of the 1.5 micron microdiscs has traversed and pulmonary circulation and had been trapped predominantly in the liver and kidney ("relative activities" of 1.10±0.21 and 0.091±0.017 respectively). Unlike the 3 micron microdiscs, the 1.5 micron microdiscs could not be detected in the samples of bowel, skeletal muscle and brain (in spite of an approximately ten fold increase in the administered activity per unit body weight compared with Experiment 1 and an approximately 25 fold increase compared with Experiment 2). These vascular beds appear to allow the passage of the 1.5 micron discs. There was no evidence of clumping of microdiscs—all of the 25 discs found were single discs and were not in direct close association with additional microdiscs.

TABLE 1

Summary of Experimental Details and Microdisc Characteristics

| | Microdiscs used: 0.7 μm thick | | |
|---|---|---|---|
| Quantity | 3 μm squares | 3 μm squares | 1.5 μm circles |
| Fraction of activity extracted and injected | 0.8 | 0.8 | 0.93 |
| Number of microdiscs | $2.88 \cdot 10^8$ | $2.88 \cdot 10^8$ | $1.14 \cdot 10^9$ |
| Activity injected (uCi) | 18.4 | 8 | 110 |
| Animal weight (kg) | 45 | 48 | 21 |
| Projected tissue activity (cps/g) | 15.5 | 6.16 | 194 |
| Estimated blood volume (1)* | 2.88 | 3.02 | 1.65 |
| Projected blood activity (cps/ml) | 249 | 98 | 2462 |

*Estimated from formula presented in (7)
Blood Volume (1) = 0.179 (body weight (kg) **0.73
Assuming instantaneous uniform mixing and no trapping of the microdisc

TABLE 2

Activity of whole blood in cps/ml above background as a function of time after administration of microdiscs. Background was 5.5 cps for Experiment 1 and 2 cps for Experiments 2 and 3.

| Time after injection (mins) | 3 μm squares | 3 μm discs | 1.5 μm discs |
|---|---|---|---|
| 1 | | | 23.4 |
| 2 | 5.5 | 5.3 | 16.6 |
| 3 | | | 13.27 |
| 4 | 2.4 | 3.7 | 11.98 |
| 5 | | | 10.6 |
| 6 | 1.6 | 3.5 | |
| 7 | | | 9.9 |
| 8 | 1.9 | 2.9 | |
| 9 | | | 9.4 |
| 10 | 1.5 | 2.9 | |
| 11 | | | 9.0 |
| 12 | 1.6 | 2.5 | |
| 13 | | | 8.3 |
| 14 | 1.5 | 2.8 | |
| 15 | | | 7.6 |
| 16 | 1.8 | 2.6 | |
| 17 | | | 7.6 |
| 18 | 1.8 | 2.2 | |
| 19 | | | 7.3 |
| 20 | 1.8 | 2.5 | |
| 22 | 1.6 | 2.3 | |
| 24 | 1.6 | 2.1 | 6.9 |
| 26 | 1.4 | 2.2 | |
| 28 | 1.9 | 2.4 | |
| 29 | | | 6.8 |
| 30 | 2.1 | 2.1 | |
| 34 | | | 6.7 |
| 39 | | | 6.4 |
| 44 | | | 6.1 |
| 49 | | | 6.0 |
| 54 | | | 6.1 |
| 59 | | | 5.8 |

TABLE 3

"Relative activity" of whole blood as a function of time after injection. "Relative activity" is expressed as the level of radioactivity above background divider by the projected blood activity if the injected microspheres were uniformly and instantaneously distributed in the total blood volume (Table 1)

| Time after injection (mins) | 3 μm squares | 3 μm discs | 1.5 μm discs |
|---|---|---|---|
| 1 | | | 0.0095 |
| 2 | 0.022 | 0.0541 | 0.0067 |
| 3 | | | 0.0054 |
| 4 | 0.0096 | 0.0378 | 0.0048 |
| 5 | | | 0.0043 |
| 6 | 0.0064 | 0.0347 | |
| 7 | | | 0.0040 |
| 8 | 0.0076 | 0.0296 | |
| 9 | | | 0.0038 |
| 10 | 0.0060 | 0.0296 | |
| 11 | | | 0.0037 |
| 12 | 0.0064 | 0.0255 | |
| 13 | | | 0.0034 |
| 14 | 0.0060 | 0.0186 | |
| 15 | | | 0.0031 |
| 16 | 0.0072 | 0.0265 | |
| 17 | | | 0.0031 |
| 18 | 0.0072 | 0.0224 | |
| 19 | | | 0.0030 |
| 20 | 0.0072 | 0.0255 | |
| 22 | 0.0064 | 0.0235 | |
| 24 | 0.0064 | 0.0214 | 0.0028 |
| 26 | 0.0056 | 0.0224 | |
| 28 | 0.0076 | 0.0245 | |
| 29 | | | 0.0028 |
| 30 | 0.0084 | 0.0214 | |
| 34 | | | 0.0027 |
| 39 | | | 0.0026 |
| 44 | | | 0.0025 |
| 49 | | | 0.0024 |

TABLE 4

Activity of samples of various organs expressed as cps/gm sample weight about background

| Organ | 3 μm squares | 3 μm discs | 1.5 μm discs |
|---|---|---|---|
| Lung: | | | |
| Right Diagrammatic Lobe | 1546 | 620.8 | 16104+/−8935 |
| Right Middle Lobe | 1438 | 366.9 | 25600+/−4640 |
| Right Apical Lobe | 898 | 480.5 | 27478+/−4181 |
| Left Diagrammatic Lobe | 1893+/−141 | 61.9 | 21756+/−4100 |
| Left Middle Lobe | — | 349.3 | 21000 |
| Left Apical Lobe | 1632+/−233 | 77.8 | 9300 |
| Accessory Lobe | | 582.5 | 31941+/−6007 |
| Liver: | | | |
| Right Lateral Lobe | 6.4 | 3.5 | 238.5+/−17.5 |
| Medial Lobe | — | 3.3 | 227.5+/−15.5 |
| Left Lateral Lobe | 5.5 | 3.3 | 184+/−57 |
| Kidney: | | | |
| Right | — | 18.1 | 18+/−5 |
| Left | — | 17.1 | 17+/−3 |
| Adrenal | — | 3.6,4.3 | |
| Spleen | 7.7 | 3.3 | 300+/−71 |
| Pancreas | — | 2.6 | |
| Heart: | | | |
| Left Ventricle | — | 1.7 | 6.8+/−0.7 |
| Right Ventricle | 2.3 | 1.9 | 10+/−4 |
| Small Bowel | — | 2.6 | 0.0 |
| Colon | — | 1.2 | 0.0 |
| Skeletal Muscle | — | 0.8 | 0.0 |
| Brain: | | | |
| Cerebral Hemispheres | — | 0.6 | 0.0 |

— means that no measurement has been made.

TABLE 5

"Relative activity" of various organs, expressed as a ratio of tissue activity (cps above background/g sample weight) to the total injected activity divided by the body weight.

| Organ | 3 μm squares | 3 μm discs | 1.5 μm discs |
|---|---|---|---|
| Lung: | | | |
| Right Diagrammatic Lobe | 90.8+/−8.6 | 100.7 | 83.2+/−80 |
| Right Middle Lobe | 90.1+/−6.53 | 59.5 | 132+/−41.2 |
| Right Apical Lobe | 56.3+/−11 | 78.0 | 142+/−37 |
| Left Diagrammatic Lobe | 118.65 | 10.0 | 112.3+/−37 |
| Left Middle Lobe | — | 56.7 | 109+/−43 |
| Left Apical Lobe | 102+/−4.6 | 12.6 | 48.13+/−36 |
| Accessory Lobe | | 94.5 | 165+/−31 |
| Liver: | | | |
| Right Lateral Lobe | 0.401 | 0.568 | 1.23+/−0.128 |
| Medial Lobe | — | 0.535 | 1.18 |
| Left Lateral Lobe | 0.345 | 0.535 | 0.62,1.03,1.19 |
| Kidney: | | | |
| Right | — | 2.94 | 0.094+/−0.025 |
| Left | — | 2.78 | 0.088+/−0.144 |
| Adrenal | | 0.698, 0.584 | |
| Spleen | 0.48 | 0.535 | 1.55+/−0.366 |
| Pancreas | — | 0.422 | |
| Heart: | | | |
| Left Ventricle | — | 0.276 | 0.035+/−0.003 |
| Right Ventricle | 0.144 | 0.308 | 0.031+/−0.02 |
| Small Bowel | — | 0.422 | 0.0 |
| Colon | — | 0.195 | 0.0 |
| Skeletal Muscle | — | 0.130 | 0.0 |
| Brain: | | | |
| Cerebral Hemispheres | | 0.100 | 0.0 |

— means that no measurement has been made.

TABLE 6

Relation between activity and blood flow

| Tissue | Relative blood flow in tissue* | Relative activity** from experiment | | |
|---|---|---|---|---|
| | | 3 μm squares | 3 μm discs | 1.5 μm discs |
| Lung | 60 | 83+/−10.5 | 52.7+/−6 | 104+/−34 |
| Skeletal muscle | 0.15 | | 0.13 | 0.0 |
| Kidney | 12 | | 2.84+/−0.08 | 0.09 |
| Heart | 6.3 | 0.126 | 0.291+/−0.016 | 0.042 |
| Brain | 4.8 | | 0.097 | 0.0 |

*Relative blood flow = (blood flow per unit mass of tissue 2.blood flow from one side of heart/mass of animal
**Relative activity = activity per unit mass of tissue (activity per unit mass if activity were uniformly distributed)

The above experimental work shows:

1. The techniques for filtering, drying and resuspending the particles work and agglomeration is not a problem;

2. There were no acute medical problems despite the fact that the doses were larger than those which would be used as a drug. This has also been reported in the literature as follows.

Chemical evaluation of acute cardiopulmonary toxicity of microspheres. D. R. Allen, J. M. Ferrens, F. W. Cheney, W B. Nelp. 1978. J. Nucl. Med. Vol. 19 No. 11 p. 1204–1208

Pulmonary perfusion imaging: Acute toxicity and safety factors as a function of particle size. M. A. Davis, R. A. Taube. 1978. J. Nucl. Med. Vol. 19 No. 11, p. 1209–1213.

Pathological changes in the lungs of mice following injection of human albumin microspheres. J. Szymendera, O. Mioduszewska, I. Licinska, A. Czarnomska, B. Lucka. 1977. J. Nucl. Med. Vol. 18 No. 5 p. 478–482.

Blood flow measurements with radiolabelled particles. M. Heyman, B. D. Payne J. I. E. Hoffman, A. M. Rudolph 1977. Prog. Cardiovascular Diseases Vol. XX No. 1 p. 55–79.

3. The data, particularly for the 1.5 um devices indicate that the removal by the circulation outside the lung, liver and spleen is small, so perfusing individual limbs or organs with blood containing MEDICs is viable.

4. To get general unrestricted circulation, coatings which will prevent attack by the recticulendothelia system are needed.

We claim:

1. An intravascular implant comprising a plurality of microelectronic devices each encapsulating a pharmaceutical compound or composition and each having a maximum dimension of less than 500 μm and adapted to pass through a body along blood vessels in large numbers, each device incorporating signal processing means for providing an output in response to an input signal, said output of said signal processing means causing rupture of said device and release of said pharmaceutical compound or composition into said body.

2. The implant of claim 1 wherein said devices are less then 7 μm in maximum dimension.

3. The implant of claim 2 wherein each device includes piezo electric material and rectifying means cooperating with said piezo electric material for generating an electric signal.

4. The implant of claim 1 wherein said devices are less than 3 μm in maximum dimension.

5. The implant of claim 1 wherein said input signal is acoustic.

6. The implant of claim 1 wherein said input signal is electromagnetic.

7. The implant of claim 1 wherein said input signal is representative of temperature.

8. The implant of claim 7 wherein said signal processing means includes a diode having electrical characteristics which vary with temperature and thereby provide said input signal representative of temperature.

9. The implant of claim 1 wherein said input signal is representative of pH value.

10. The implant of claim 9 wherein said signal processing means includes a chemically sensitive field effect transistor for measuring pH values thereby providing said input signal representative of pH value.

11. The implant of claim 1 wherein the input signal is chemical.

12. The implant of claim 1 wherein the output is acoustic.

13. The implant of claim 1 wherein the output is electromagnetic.

14. The implant of claim 1 wherein the output is chemical.

15. The implant of claim 1 wherein each device includes a battery.

16. The implant of claim 1 wherein each device further comprises an antibody coating.

17. A pharmaceutical preparation comprising a plurality of semiconductor devices in a pharmaceutically acceptable carrier or diluent, each device having a maximum dimension less than 500 μm and encapsulating a pharmaceutical compound or composition and adapted to pass along blood vessels in large numbers, said devices each including signal processing means for providing an output in response to an input signal, each said device having a frangible part which is capable of rupturing to release said pharmaceutical compound or compositon from each said device on receipt of said output from each said signal processing means.

18. The preparation of claim 17 wherein each device comprises a chemically sensitive field effect transistor for measuring pH values to provide said input signal.

19. The preparation of claim 17 wherein said signal processing means includes a diode for measuring temperature to provide said input signal.

20. A method of treating the animal or human body comprising administering a pharmaceutical preparation into the vascular system in an amount effective to treat the body, said pharmaceutical preparation comprising a plurality of semiconductor devices in a pharmaceutically acceptable carrier or diluent, each device having a maximum diameter less than 500 μm and encapsulating a pharmaceutical compound or composition and adapted to pass along blood vessels in large numbers, each of said devices including signal processing means for providing an output in response to an input signal, each of said devices having a frangible part which is capable of rupturing to release said pharmaceutical compound or composition on receipt of said output from each said signal processing means.

21. The method of claim 20 wherein the body is selectively subject to electromagnetic, or ionizing radiation, or acoustic energy to provide said input signal to said signal processing means to obtain release of said pharmaceutical compound or composition in a selected part of said body.

22. A method of detecting a body function in an animal or human body comprising the steps of: inserting or inhaling into a body part a pharmaceutical composition comprising a pharmaceutically acceptable carrier or diluent containing a plurality of intravascular devices, each device having a maximum dimension less than 500 microns and adapted to pass along blood vessels, each device including signal processing means for providing an output in response to an input signal; providing an input signal to each said intravascular device; and obtaining an output response from at least a plural subset from among the plurality of intravascular devices.

23. The method of claim 22 wherein the body is selectively subjected to an electromagnetic or ionizing radiation, or acoustic energy to provide said input signal.

24. The method of claim 22 wherein said intravascular devices are subject to a temperature, pH or chemical range to provide said input signal.

25. The method of claim 22 wherein said output is acoustic, electromagnetic, or chemical.

26. The method of claim 22 wherein said pharmaceutically acceptable carrier is a volatile liquid wherein said step of inhaling includes the step of administering by inhalation as a gas.

27. A method of delivering a drug substance to a predetermined body site of an animal or a human body comprising the steps of:

administering to said animal or human a pharmaceutical composition of a pharmaceutical carrier or diluent containing an intravascular microdisc device having a maximum dimension less than 500 microns adapted to pass along blood vessels, said device including said drug substance, and signal processing means for releasing said drug substance in response to an input signal; and providing said input signal thereby releasing said drug substance for said intravascular device.

28. The delivery method of claim 27 wherein said input signal is electromagnetic, or ionizing radiation, or acoustic energy.

* * * * *